US012124668B2

(12) United States Patent
Arney et al.

(10) Patent No.: US 12,124,668 B2
(45) Date of Patent: Oct. 22, 2024

(54) METHODS AND USER INTERFACES FOR TRACKING EXECUTION TIMES OF CERTAIN FUNCTIONS

(71) Applicant: Apple Inc., Cupertino, CA (US)

(72) Inventors: Julie A. Arney, Los Gatos, CA (US); Gary I. Butcher, Los Gatos, CA (US); Edward Chao, Palo Alto, CA (US); Brett L. Lareau, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/550,806

(22) Filed: Dec. 14, 2021

(65) Prior Publication Data
US 2022/0374106 A1      Nov. 24, 2022

Related U.S. Application Data

(60) Provisional application No. 63/191,870, filed on May 21, 2021.

(51) Int. Cl.
*G06F 3/0481* (2022.01)
*A63B 24/00* (2006.01)
(Continued)

(52) U.S. Cl.
CPC ........ *G06F 3/0481* (2013.01); *A63B 24/0062* (2013.01); *A63B 71/0622* (2013.01);
(Continued)

(58) Field of Classification Search
CPC .... G06F 3/048; G06F 3/0481; G06F 3/04842; G06F 3/0488–04886; G06F 3/165;
(Continued)

(56) References Cited

U.S. PATENT DOCUMENTS 7,199,700 B1    4/2007  Mcpherson et al.
8,562,489 B2 *  10/2013 Burton .................. G04G 9/007
                                                      482/901
(Continued)

FOREIGN PATENT DOCUMENTS

CN    101822894 A    9/2010
CN    102488501 A    6/2012
(Continued)

OTHER PUBLICATIONS

Daniel About Tech, Workout App Full Review, Feb. 19, 2019, Youtube. <https://www.youtube.com/watch?v=aHXCNfSccoY> (Year: 2019).*

(Continued)

*Primary Examiner* — Liang Y Li
(74) *Attorney, Agent, or Firm* — DLA Piper LLP (US)

(57) ABSTRACT

The present disclosure generally relates to methods and user interfaces for recording the execution duration of functions. In some embodiments, methods and user interfaces for recording the execution duration of functions are described. In some embodiments, methods and user interfaces for recording the execution duration of two or more related functions, wherein execution of the two or more functions can be initiated from a single user interface, are described. In some embodiments, methods and user interfaces for recording the execution duration of functions, wherein the related functions are associated with mindfulness, are described.

54 Claims, 16 Drawing Sheets

(51) Int. Cl.
  *A63B 71/06* (2006.01)
  *G04G 9/00* (2006.01)
  *G06F 3/04842* (2022.01)
  *G06F 3/0488* (2022.01)
  *G06F 3/16* (2006.01)

(52) U.S. Cl.
  CPC ......... *G04G 9/007* (2013.01); *G06F 3/04842* (2013.01); *G06F 3/0488* (2013.01); *G06F 3/165* (2013.01)

(58) Field of Classification Search
  CPC ......... A63B 24/0062; A63B 2024/0065–0071; A63B 71/0619–0672; A63B 71/0622; A63B 2071/0625–0633; G04G 9/007; G16H 20/30
  See application file for complete search history.

(56) References Cited

U.S. PATENT DOCUMENTS

| | | | |
|---|---|---|---|
| 10,080,530 B2* | 9/2018 | Cheng | A61B 5/7455 |
| 11,931,625 B2* | 3/2024 | D'Auria | H04N 7/155 |
| 2003/0171643 A1 | 9/2003 | Noguchi et al. | |
| 2004/0254501 A1 | 12/2004 | Mault | |
| 2005/0165609 A1 | 7/2005 | Zuberec et al. | |
| 2007/0129883 A1 | 6/2007 | Kuo et al. | |
| 2007/0208269 A1 | 9/2007 | Mumford et al. | |
| 2008/0072902 A1 | 3/2008 | Setzer et al. | |
| 2008/0319279 A1 | 12/2008 | Ramsay et al. | |
| 2009/0024047 A1 | 1/2009 | Shipley et al. | |
| 2009/0227425 A1 | 9/2009 | Shirasaki et al. | |
| 2009/0263773 A1 | 10/2009 | Kotlyar et al. | |
| 2009/0322686 A1 | 12/2009 | Jayasinghe | |
| 2010/0035669 A1 | 2/2010 | Jang et al. | |
| 2010/0069774 A1 | 3/2010 | Bingham et al. | |
| 2010/0095961 A1 | 4/2010 | Tornesel et al. | |
| 2010/0273610 A1* | 10/2010 | Johnson | A61B 5/11 482/9 |
| 2010/0331145 A1 | 12/2010 | Lakovic et al. | |
| 2012/0015778 A1* | 1/2012 | Lee | A63B 71/0686 482/8 |
| 2013/0139107 A1 | 5/2013 | Jung | |
| 2013/0333703 A1 | 12/2013 | Wallace et al. | |
| 2014/0018049 A1 | 1/2014 | Cannon et al. | |
| 2014/0316191 A1 | 10/2014 | De Zambotti et al. | |
| 2014/0344375 A1 | 11/2014 | Hauser et al. | |
| 2015/0096564 A1 | 4/2015 | Cosnek | |
| 2015/0238722 A1 | 8/2015 | Al-Ali | |
| 2015/0283337 A1 | 10/2015 | Adams et al. | |
| 2015/0342518 A1 | 12/2015 | Persidsky et al. | |
| 2016/0007911 A1 | 1/2016 | Wu et al. | |
| 2016/0058337 A1* | 3/2016 | Blahnik | A61B 5/1112 600/595 |
| 2016/0114213 A1 | 4/2016 | Lee | |
| 2017/0243508 A1* | 8/2017 | Cheng | G09B 5/02 |
| 2017/0332972 A1 | 11/2017 | Nagasaki et al. | |
| 2017/0354795 A1* | 12/2017 | Blahnik | G06F 3/011 |
| 2018/0329584 A1* | 11/2018 | Williams | H04L 67/12 |
| 2019/0320939 A1 | 10/2019 | Orvis et al. | |
| 2020/0149921 A1 | 5/2020 | Hoffman et al. | |
| 2020/0265744 A1* | 8/2020 | Lim | G06F 3/015 |
| 2021/0113116 A1 | 4/2021 | Chen et al. | |
| 2021/0286502 A1 | 9/2021 | Lemay et al. | |
| 2021/0338971 A1 | 11/2021 | Blahnik et al. | |
| 2022/0080261 A1* | 3/2022 | Li | A63B 24/0062 |
| 2023/0306695 A1 | 9/2023 | Rockel et al. | |
| 2023/0347104 A1 | 11/2023 | Blahnik et al. | |

FOREIGN PATENT DOCUMENTS

| | | | |
|---|---|---|---|
| EP | 2311533 A1 | 4/2011 | |
| EP | 2866103 A2 | 4/2015 | |
| JP | 2003-305094 A | 10/2003 | |
| JP | 2007-190275 A | 8/2007 | |
| JP | 2007-190276 A | 8/2007 | |
| JP | 2009119068 A * | 6/2009 | |
| JP | 2010-104456 A | 5/2010 | |
| JP | 2010-533541 A | 10/2010 | |
| JP | 2012-19852 A | 2/2012 | |
| JP | 2012-35055 A | 2/2012 | |
| JP | 2012-524638 A | 10/2012 | |
| JP | 2012-524639 A | 10/2012 | |
| JP | 2013-131215 A | 7/2013 | |
| JP | 2018-504159 A | 2/2018 | |
| KR | 10-2010-0024503 A | 3/2010 | |
| KR | 10-2013-0142412 A | 12/2013 | |
| KR | 10-2014-0138361 A | 12/2014 | |
| WO | 2004/082751 A1 | 9/2004 | |
| WO | 2005/018737 A1 | 3/2005 | |
| WO | 2008/110956 A1 | 9/2008 | |
| WO | 2009/002577 A1 | 12/2008 | |
| WO | 2012/117376 A1 | 9/2012 | |
| WO | 2014/107795 A1 | 7/2014 | |
| WO | 2015/039979 A1 | 3/2015 | |
| WO | WO-2018209152 A1 * | 11/2018 | G06F 1/163 |

OTHER PUBLICATIONS

AllThingsGizmo, How to Multitask on the AppleWatch, Jul. 12, 2015, Youtube. <https://www.youtube.com/watch?v=Mxt2tfABwLg> (Year: 2015).*
Advisory Action received for U.S. Appl. No. 15/372,133, mailed on Aug. 28, 2019, 7 pages.
Advisory Action received for U.S. Appl. No. 15/372,133, mailed on Jun. 2, 2020, 5 pages.
Applicant-Initiated Interview Summary received for U.S. Appl. No. 15/372,133, mailed on Dec. 23, 2019, 6 pages.
Applicant-Initiated Interview Summary received for U.S. Appl. No. 15/372,133, mailed on May 4, 2020, 5 pages.
Applicant-Initiated Interview Summary received for U.S. Appl. No. 15/372,133, mailed on Nov. 12, 2020, 5 pages.
Benson Amanda, "Health App of the Month: Move, The Daily Activity Reminder", ThinkHealth, Retrieved from the internet: https://thinkhealth.priorityhealth.com/health-app-of-the-month-move-the-daily-activity-reminder/, Mar. 12, 2015, pp. 1-4.
Breathe Deeply Now! for Windows Phone Version, Online Available at: https://www.appx4fun.com/apps/5402/, Feb. 15, 2015, 11 pages.
Decision to Grant received for Danish Patent Application No. PA201770384, mailed on Jun. 28, 2019, 2 pages.
Extended European Search Report received for European Patent Application No. 17810736.3, mailed Nov. 7, 2019, 10 pages.
Final Office Action received for U.S. Appl. No. 15/372,133, mailed on Apr. 6, 2020, 16 pages.
Final Office Action received for U.S. Appl. No. 15/372,133, mailed on Apr. 18, 2019, 14 pages.
Intention to Grant received for Danish Patent Application No. PA201770384, mailed on Mar. 13, 2019, 2 pages.
Intention to Grant received for Danish Patent Application No. PA201770384, mailed on Nov. 14, 2018, 2 pages.
International Preliminary Report on Patentability received for PCT Patent Application No. PCT/US2017/035309, mailed on Dec. 20, 2018, 28 pages.
International Search Report and Written Opinion received for PCT Patent Application No. PCT/US2017/035309, mailed on Sep. 27, 2017, 31 pages.
Invitation to Pay Additional Fee received for PCT Patent Application No. PCT/US2017/035309, mailed on Jul. 14, 2017, 2 pages.
Non-Final Office Action received for U.S. Appl. No. 15/372,133, mailed on Jul. 24, 2018, 13 pages.
Non-Final Office Action received for U.S. Appl. No. 15/372,133, mailed on Oct. 3, 2019, 14 pages.
Non-Final Office Action received for U.S. Appl. No. 15/372,133, mailed on Sep. 14, 2020, 17 pages.
Notice of Acceptance received for Australian Patent Application No. 2017277848, mailed on Apr. 20, 2020, 3 pages.
Notice of Acceptance received for Australian Patent Application No. 2020203453, mailed on Feb. 10, 2021, 3 pages.

(56) References Cited

OTHER PUBLICATIONS

Notice of Allowance received for Chinese Patent Application No. 201710400594.9, mailed on Jul. 30, 2020, 2 pages (1 page of English Translation and 1 page of Official Copy).
Notice of Allowance received for Japanese Patent Application No. 2018-563158, mailed on Nov. 8, 2019, 4 pages (1 page of English Translation and 3 pages of Official Copy).
Notice of Allowance received for Japanese Patent Application No. 2019-222213, mailed on Aug. 30, 2021, 4 pages (1 page of English Translation and 3 pages of Official Copy).
Notice of Allowance received for Korean Patent Application No. 10-2018-7034689, mailed on Mar. 27, 2020, 6 pages (2 pages of English Translation and 4 pages of Official Copy).
Notice of Allowance received for Korean Patent Application No. 10-2020-7016741, mailed on Feb. 24, 2021, 5 pages (2 pages of English Translation and 3 pages of Official Copy).
Notice of Allowance received for U.S. Appl. No. 15/372,133, mailed on Feb. 11, 2021, 8 pages.
Notice of Allowance received for U.S. Appl. No. 15/372,133, mailed on Feb. 26, 2021, 3 pages.
Office Action received for Australian Patent Application No. 2017277848, mailed on Aug. 28, 2019, 4 pages.
Office Action received for Australian Patent Application No. 2017277848, mailed on Jan. 16, 2020, 4 pages.
Office Action received for Australian Patent Application No. 2017277848, mailed on Jun. 13, 2019, 4 pages.
Office Action received for Australian Patent Application No. 2017277848, mailed on Mar. 4, 2020, 3 pages.
Office Action received for Australian Patent Application No. 2017277848, mailed on Nov. 1, 2019, 4 pages.
Office Action received for Australian Patent Application No. 2020203453, mailed on Aug. 12, 2020, 4 pages.
Office Action received for Australian Patent Application No. 2020203453, mailed on Dec. 18, 2020, 4 pages.
Office Action received for Australian Patent Application No. 2020203453, mailed on Oct. 29, 2020, 4 pages.
Office Action received for Australian Patent Application No. 2021203301, mailed on Nov. 3, 2021, 3 pages.
Office Action received for Chinese Patent Application No. 201710400594.9, mailed on Apr. 23, 2018, 3 pages (1 page of English Translation and 2 pages of Official copy).
Office Action received for Chinese Patent Application No. 201710400594.9, mailed on Jul. 17, 2017, 2 pages (1 page of English Translation and 1 page of Official Copy).
Office Action received for Chinese Patent Application No. 201710400594.9, mailed on Mar. 20, 2020, 6 pages (3 pages of English Translation and 3 pages of Official Copy).
Office Action received for Chinese Patent Application No. 201710400594.9, mailed on May 14, 2019, 14 pages (5 pages of English Translation and 9 pages of Official Copy).
Office Action received for Chinese Patent Application No. 201710400594.9, mailed on Nov. 15, 2019, 12 pages (5 pages of English Translation and 7 pages of Official Copy).
Office Action received for Danish Patent Application No. PA201770384, mailed on Oct. 27, 2017, 7 pages.
Office Action received for European Patent Application No. 17810736.3, mailed on Nov. 11, 2020, 6 pages.
Office Action received for Japanese Patent Application No. 2019-222213, mailed on Jan. 4, 2021, 9 pages (5 pages of English Translation and 4 pages of Official Copy).
Office Action received for Korean Patent Application No. 10-2018-7034689, mailed on Nov. 28, 2019, 11 pages (5 pages of English Translation and 6 pages of Official Copy).
Office Action received for Korean Patent Application No. 10-2020-7016741, mailed on Jul. 22, 2020, 10 pages (4 pages of English Translation and 6 pages of Official Copy).
Office Action received for Korean Patent Application No. 10-2021-7015702, mailed on Jun. 19, 2021, 12 pages (6 pages of English Translation and 6 pages of Official Copy).
Paced Breathing, "How to use Paced Breathing", Retrieved from: https://pacedbreathing.blogspot.com/2014/03/how-to-use-paced-breathing.html on Sep. 9, 2020, Apr. 3, 2015, 7 pages.
Stachowiak Sandy, "Relax, breathe deep and regain focus with Hear and Now", Available online at: https://appadvice.com/appnn/2016/01/relax-breathe-deep-and-regain-focus-with-hear-and-now, Jan. 6, 2016, 3 pages.
Supplemental Notice of Allowance received for U.S. Appl. No. 15/372,133, mailed on Mar. 26, 2021, 3 pages.
Tiles and Toasts, "Toast Notification and Action Center Overview for Windows 10", Online Available at: https://blogs.msdn.microsoft.com/tiles_and_toasts/2015/07/08/toast-notification-and-action-center-overview-for-windows-10/, Published on Jul. 8, 2015, 9 pages.
Time Out app, "Release Notes". Online Available at: www.dejal.com/timeout/release, 2016, 8 pages.
Time Out app, Screens shots and user guide. Online Available at: https://web.archive.org/web/20160314023701/http://www.dejal.com/timeout/images/, Mar. 14, 2016, 10 pages.
Wesley, "Apple Watch Series 1", online available at:-http://toolbox.info/blog/archives/1737-unknown.html, May 28, 2015, 5 pages (Official copy only) See Communication under 37 CFR § 1.98(a) (3).
Windowsunited, "Breathe Deeply Now! Please Take a Deep Breath and Relax", Online Available at: https://windowsunited.de/breathe-deeply-now-die-app-gegen-angszustaende/, Published on Oct. 4, 2014, 8 pages.
Notice of Allowance received for U.S. Appl. No. 17/345,092, mailed on Apr. 10, 2023, 9 pages.
International Search Report and Written Opinion received for PCT Patent Application No. PCT/US2022/030309, mailed on Sep. 15, 2022, 14 pages.
Notice of Acceptance received for Australian Patent Application No. 2021203301, mailed on Feb. 23, 2022, 3 pages.
Notice of Allowance received for Korean Patent Application No. 10-2021-7015702, mailed on Dec. 27, 2021, 3 pages (Official Copy Only) See Communication under 37 CFR § 1.98(a) (3).
Office Action received for Australian Patent Application No. 2021203301, mailed on Jan. 18, 2022, 3 pages.
Office Action received for Korean Patent Application No. 10-2022-7010343, mailed on May 19, 2022, 12 pages (6 pages of English Translation and 6 pages of Official Copy).
Office Action received for Korean Patent Application No. 10-2022-7010343, mailed on Nov. 17, 2022, 6 pages (3 pages of English Translation and 3 pages of Official Copy).
Gil, Lory, "How to Use the Activity and Workout Apps on Apple Watch", Online Available at: https://www.macrumors.com/how-to/apple-watch-activity-workout-apps/, May 4, 2015, 5 pages.
Iphonetricks.org, "Apple Watch Activity App Setup & Usage Tips", Online Available at: https://www.iphonetricks.org/apple-watch-activity-app-setup-usage-tips/, May 4, 2015, 4 pages.
Non-Final Office Action received for U.S. Appl. No. 17/345,092, mailed on Jan. 25, 2023, 36 pages.
Office Action received for Japanese Patent Application No. 2021-159616, mailed on Dec. 5, 2022, 11 pages (6 pages of English Translation and 5 pages of Official Copy).
Applicant-Initiated Interview Summary received for U.S. Appl. No. 17/345,092, mailed on Feb. 28, 2023, 5 pages.
Notice of Allowance received for Korean Patent Application No. 10-2022-7010343, mailed on Feb. 27, 2023, 6 pages (2 pages of English Translation and 4 pages of Official Copy).
Extended European Search Report received for European Patent Application No. 23216678.5, mailed on Mar. 7, 2024, 10 pages.
Hang et al., "Oh App, Where Art Thou? On App Launching Habits of Smartphone Users", Proceedings of the 15th international conference on Human-computer interaction with mobile devices and services, MobileHCI '13, Online available at: https://dl.acm.org/doi/10.1145/2493190.2493219, Aug. 27-30, 2013, 4 pages.
Office Action received for Chinese Patent Application No. 202011096049.3, mailed on Nov. 3, 2023, 27 pages (12 pages of English Translation and 15 pages of Official Copy).
Wikipedia, "Nike+iPod", Online available at: http://en.wikipedia.org/w/index.php?title=Nike%2BiPod&oldid=420671395, Mar. 25, 2011, pp. 1-4.

(56) References Cited

OTHER PUBLICATIONS

Zou et al., "Prophet: What App You Wish to Use Next", UbiComp '13, Online available at: DOI: 10.1145/2494091.2494146, Sep. 8-12, 2013, pp. 167-170.

Decision to Grant received for European Patent Application No. 17810736.3, mailed on Jan. 5, 2024, 2 pages.

Office Action received for Japanese Patent Application No. 2021-159616, mailed on Dec. 8, 2023, 4 pages (2 pages of English Translation and 2 pages of Official Copy).

Office Action received for Japanese Patent Application No. 2021-159616, mailed on Jun. 9, 2023, 4 pages (2 pages of English Translation and 2 pages of Official Copy).

Intention to Grant received for European Patent Application No. 17810736.3, mailed on Aug. 8, 2023, 8 pages.

International Preliminary Report on Patentability received for PCT Patent Application No. PCT/US2022/030309, mailed on Nov. 30, 2023, 10 pages.

International Search Report and Written Opinion received for PCT Patent Application No. PCT/US2023/015826, mailed on Jul. 31, 2023, 18 pages.

Invitation to Pay Additional Fees and Partial International Search Report received for PCT Patent Application No. PCT/US2023/015826, mailed on Jun. 7, 2023, 10 pages.

Notice of Allowance received for Korean Patent Application No. 10-2023-7018493, mailed on Jul. 18, 2023, 7 pages (2 pages of English Translation and 5 pages of Official Copy).

Notice of Allowance received for Japanese Patent Application No. 2021-159616, mailed on Apr. 12, 2024, 4 pages (1 page of English Translation and 3 pages of Official Copy).

Office Action received for Chinese Patent Application No. 202011098154.0, mailed on Dec. 26, 2023, 22 pages (11 pages of English Translation and 11 pages of Official Copy).

Notice of Allowance received for Chinese Patent Application No. 202011096049.3, mailed on Mar. 20, 2024, 2 pages (1 page of English Translation and 1 page of Official Copy).

Office Action received for Chinese Patent Application No. 202011096049.3, mailed on Jan. 9, 2024, 8 pages (4 pages of English Translation and 4 pages of Official Copy).

Issued by the Korean Patent Office in related Patent Application No. 10-2021-7015702 on Dec. 27, 2021.

\* cited by examiner

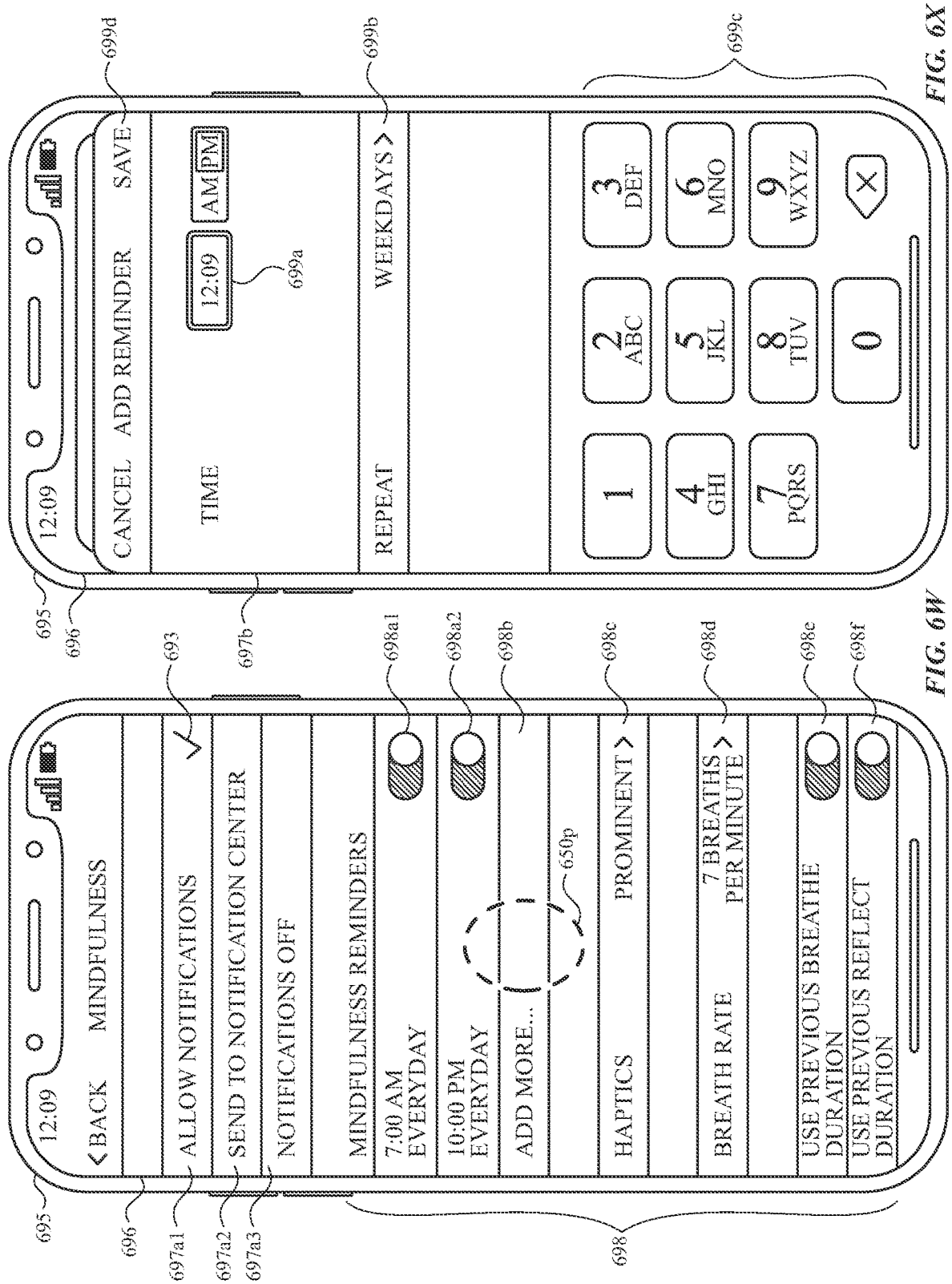

700 ⤵

702
Display, via the display generation component, a first user interface that concurrently includes:

a first user-interactive graphical user interface object that, when selected, initiates execution of a first function, wherein the first function includes measuring, via the one or more sensors, a first physiological parameter; and a second user-interactive graphical user interface object that, when selected, initiates execution of a second function different from the first function, wherein the second function includes measuring, via the one or more sensors, a second physiological parameter.

704
Receive, via the one or more input devices, a first set of one or more inputs that includes a first input corresponding to the first user-interactive graphical user interface object.

706
In response to receiving the first set of one or more inputs, execute the first function.

708
After executing the first function, display a second user interface that includes a visual representation of a first duration of time, where the first duration of time includes a first amount of cumulative time that the first function has been executed within a predetermined time period and a second amount of cumulative time that the second function has been executed during the predetermined time period.

*FIG. 7*

METHODS AND USER INTERFACES FOR TRACKING EXECUTION TIMES OF CERTAIN FUNCTIONS

CROSS-REFERENCE TO RELATED APPLICATIONS

This application claims priority to U.S. Provisional Patent Application No. 63/191,870, entitled "METHODS AND USER INTERFACES FOR TRACKING EXECUTION TIMES OF CERTAIN FUNCTIONS," filed on May 21, 2021, the content of which is hereby incorporated by reference in its entirety.

FIELD

The present disclosure relates generally to computer user interfaces, and more specifically to techniques for recording the execution duration of functions.

BACKGROUND

Personal electronic devices allow users to execute functions. Executing some functions on personal electronic devices includes recording the amount of time for which a given function has executed.

BRIEF SUMMARY

Some techniques for recording the execution duration of functions using electronic devices, however, are generally cumbersome and inefficient. For example, some existing techniques use a complex and time-consuming user interface, which may include multiple key presses or keystrokes, particularly when providing the execution duration for related, but separate functions. Existing techniques require more time than necessary, wasting user time and device energy. This latter consideration is particularly important in battery-operated devices.

Accordingly, the present technique provides electronic devices with faster, more efficient methods and interfaces for recording the execution duration of functions. Such methods and interfaces optionally complement or replace other methods for recording the execution duration of functions. Such methods and interfaces reduce the cognitive burden on a user and produce a more efficient human-machine interface. For battery-operated computing devices, such methods and interfaces conserve power and increase the time between battery charges.

In accordance with some embodiments, a method performed at a computer system that is in communication with a display generation component, one or more input devices, and one or more sensors is described. The method comprises: displaying, via the display generation component, a first user interface that concurrently includes: a first user-interactive graphical user interface object that, when selected, initiates execution of a first function, wherein the first function includes measuring, via the one or more sensors, a first physiological parameter; and a second user-interactive graphical user interface object that, when selected, initiates execution of a second function different from the first function, wherein the second function includes measuring, via the one or more sensors, a second physiological parameter; receiving, via the one or more input devices, a first set of one or more inputs that includes a first input corresponding to the first user-interactive graphical user interface object; in response to receiving the first set of one or more inputs, executing the first function; and after executing the first function, displaying a second user interface that includes a visual representation of a first duration of time, wherein the first duration of time includes a first amount of cumulative time that the first function has been executed within a predetermined time period and a second amount of cumulative time that the second function has been executed during the predetermined time period.

In accordance with some embodiments, a non-transitory computer-readable storage medium is described. The non-transitory computer-readable storage medium stores one or more programs configured to be executed by one or more processors of a computer system that is in communication with a display generation component, one or more input devices, and one or more sensors, the one or more programs including instructions for: displaying, via the display generation component, a first user interface that concurrently includes: a first user-interactive graphical user interface object that, when selected, initiates execution of a first function, wherein the first function includes measuring, via the one or more sensors, a first physiological parameter; and a second user-interactive graphical user interface object that, when selected, initiates execution of a second function different from the first function, wherein the second function includes measuring, via the one or more sensors, a second physiological parameter; receiving, via the one or more input devices, a first set of one or more inputs that includes a first input corresponding to the first user-interactive graphical user interface object; in response to receiving the first set of one or more inputs, executing the first function; and after executing the first function, displaying a second user interface that includes a visual representation of a first duration of time, wherein the first duration of time includes a first amount of cumulative time that the first function has been executed within a predetermined time period and a second amount of cumulative time that the second function has been executed during the predetermined time period.

In accordance with some embodiments, a transitory computer-readable storage medium is described. The transitory computer-readable storage medium stores one or more programs configured to be executed by one or more processors of a computer system that is in communication with a display generation component, one or more input devices, and one or more sensors, the one or more programs including instructions for: displaying, via the display generation component, a first user interface that concurrently includes: a first user-interactive graphical user interface object that, when selected, initiates execution of a first function, wherein the first function includes measuring, via the one or more sensors, a first physiological parameter; and a second user-interactive graphical user interface object that, when selected, initiates execution of a second function different from the first function, wherein the second function includes measuring, via the one or more sensors, a second physiological parameter; receiving, via the one or more input devices, a first set of one or more inputs that includes a first input corresponding to the first user-interactive graphical user interface object; in response to receiving the first set of one or more inputs, executing the first function; and after executing the first function, displaying a second user interface that includes a visual representation of a first duration of time, wherein the first duration of time includes a first amount of cumulative time that the first function has been executed within a predetermined time period and a second amount of cumulative time that the second function has been executed during the predetermined time period.

In accordance with some embodiments, a computer system is described. The computer system is in communication with a display generation component, one or more input devices, and one or more sensors, the computer system comprising: one or more processors; and memory storing one or more programs configured to be executed by the one or more processors, the one or more programs including instructions for: displaying, via the display generation component, a first user interface that concurrently includes: a first user-interactive graphical user interface object that, when selected, initiates execution of a first function, wherein the first function includes measuring, via the one or more sensors, a first physiological parameter; and a second user-interactive graphical user interface object that, when selected, initiates execution of a second function different from the first function, wherein the second function includes measuring, via the one or more sensors, a second physiological parameter; receiving, via the one or more input devices, a first set of one or more inputs that includes a first input corresponding to the first user-interactive graphical user interface object; in response to receiving the first set of one or more inputs, executing the first function; and after executing the first function, displaying a second user interface that includes a visual representation of a first duration of time, wherein the first duration of time includes a first amount of cumulative time that the first function has been executed within a predetermined time period and a second amount of cumulative time that the second function has been executed during the predetermined time period.

In accordance with some embodiments, a computer system is described. The computer system is in communication with a display generation component, one or more input devices, and one or more sensors, the computer system comprising: means for displaying, via the display generation component, a first user interface that concurrently includes: a first user-interactive graphical user interface object, that, when selected, initiates execution of a first function, wherein the first function includes measuring, via the one or more sensors, a first physiological parameter; and a second user-interactive graphical user interface object that, when selected, initiates execution of a second function different from the first function, wherein the second function includes measuring, via the one or more sensors, a second physiological parameter; means for receiving, via the one or more input devices, a first set of one or more inputs that includes a first input corresponding to the first user-interactive graphical user interface object; means, responsive to receiving the first set of one or more inputs, for executing the first function; and means, after executing the first function, displaying a second user interface that includes a visual representation of a first duration of time, wherein the first duration of time includes a first amount of cumulative time that the first function has been executed within a predetermined time period and a second amount of cumulative time that the second function has been executed during the predetermined time period.

In accordance with some embodiments, a computer program product is described. The computer program product comprises one or more programs configured to be executed by one or more processors of a computer system that is in communication with a display generation component and one or more input devices, the one or more programs including instructions for: displaying, via the display generation component, a first user interface that concurrently includes: a first user-interactive graphical user interface object that, when selected, initiates execution of a first function, wherein the first function includes measuring, via the one or more sensors, a first physiological parameter; and a second user-interactive graphical user interface object that, when selected, initiates execution of a second function different from the first function, wherein the second function includes measuring, via the one or more sensors, a second physiological parameter; receiving, via the one or more input devices, a first set of one or more inputs that includes a first input corresponding to the first user-interactive graphical user interface object; in response to receiving the first set of one or more inputs, executing the first function; and after executing the first function, displaying a second user interface that includes a visual representation of a first duration of time, wherein the first duration of time includes a first amount of cumulative time that the first function has been executed within a predetermined time period and a second amount of cumulative time that the second function has been executed during the predetermined time period.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for recording the execution duration of functions, thereby increasing the effectiveness, efficiency, and user satisfaction with such devices. Such methods and interfaces may complement or replace other methods for recording the execution duration of functions.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 7 is a flow diagram illustrating a method for recording the execution duration of functions using a computer system in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for recording the execution duration of functions. For example, there is a need for devices that enable an intuitive and efficient method for conveying a total amount of time during which two different but related functions have executed within a threshold time period on an electronic device. Such techniques can reduce the cognitive burden on a user who reviews time spent executing functions on their devices, thereby enhancing productivity. Further, such techniques can reduce processor and battery power otherwise wasted on redundant user inputs.

Below. FIGS. 1A-1B, 2, 3, 4A-4B, and 5A-5B provide a description of exempla devices for performing the techniques for managing event notifications.

Figures 6A, 6B:
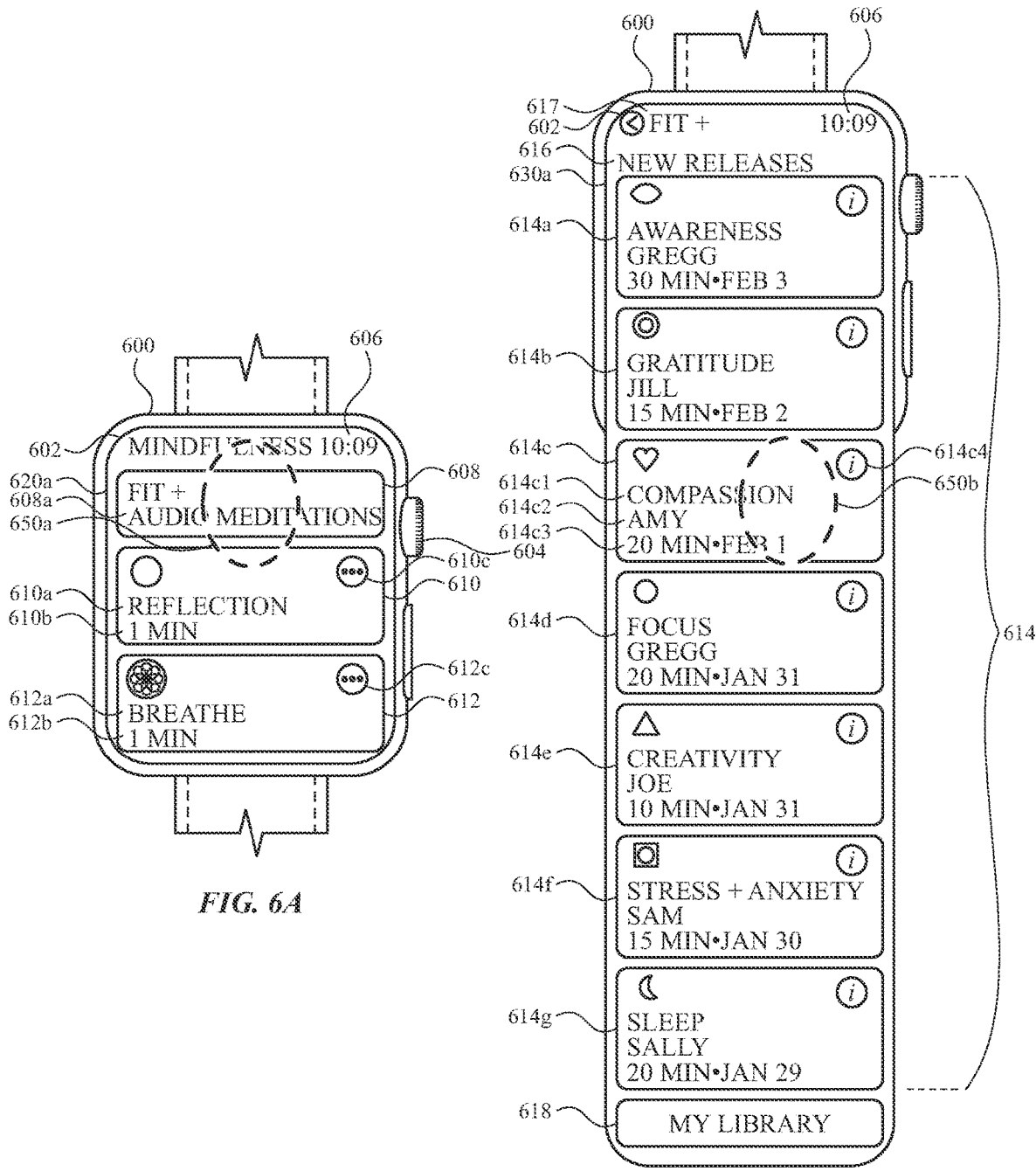
FIGS. 6A-6X illustrate exemplary user interfaces for recording the execution duration of functions.

FIGS. 6A-6X: illustrate exemplary user interfaces for recording the execution duration of functions. FIG. 7 is a flow diagram illustrating methods of managing event notifications in accordance with some embodiments. The user interfaces in FIGS. 6A-6X are used to illustrate the processes described below, including the processes in FIG. 7.

The processes described below enhance the operability of the devices and make the user-device interfaces more efficient (e.g., by helping the user to provide proper inputs and reducing user mistakes when operating/interacting with the device) through various techniques, including by providing improved visual feedback to the user, reducing the number of inputs needed to perform an operation, providing additional control options without cluttering the user interface with additional displayed controls, performing an operation when a set of conditions has been met without requiring further user input, and/or additional techniques. These techniques also reduce power usage and improve battery life of the device by enabling the user to use the device more quickly and efficiently.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. In some embodiments, these terms are used to distinguish one element from another. For example, a first touch could be termed a second touch, and, similarly, a second touch could be termed a first touch, without departing from the scope of the various described embodiments. In some embodiments, the first touch and the second touch are two separate references to the same touch. Iii some embodiments, the first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as and/or music player functions. Exemplary embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad), In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
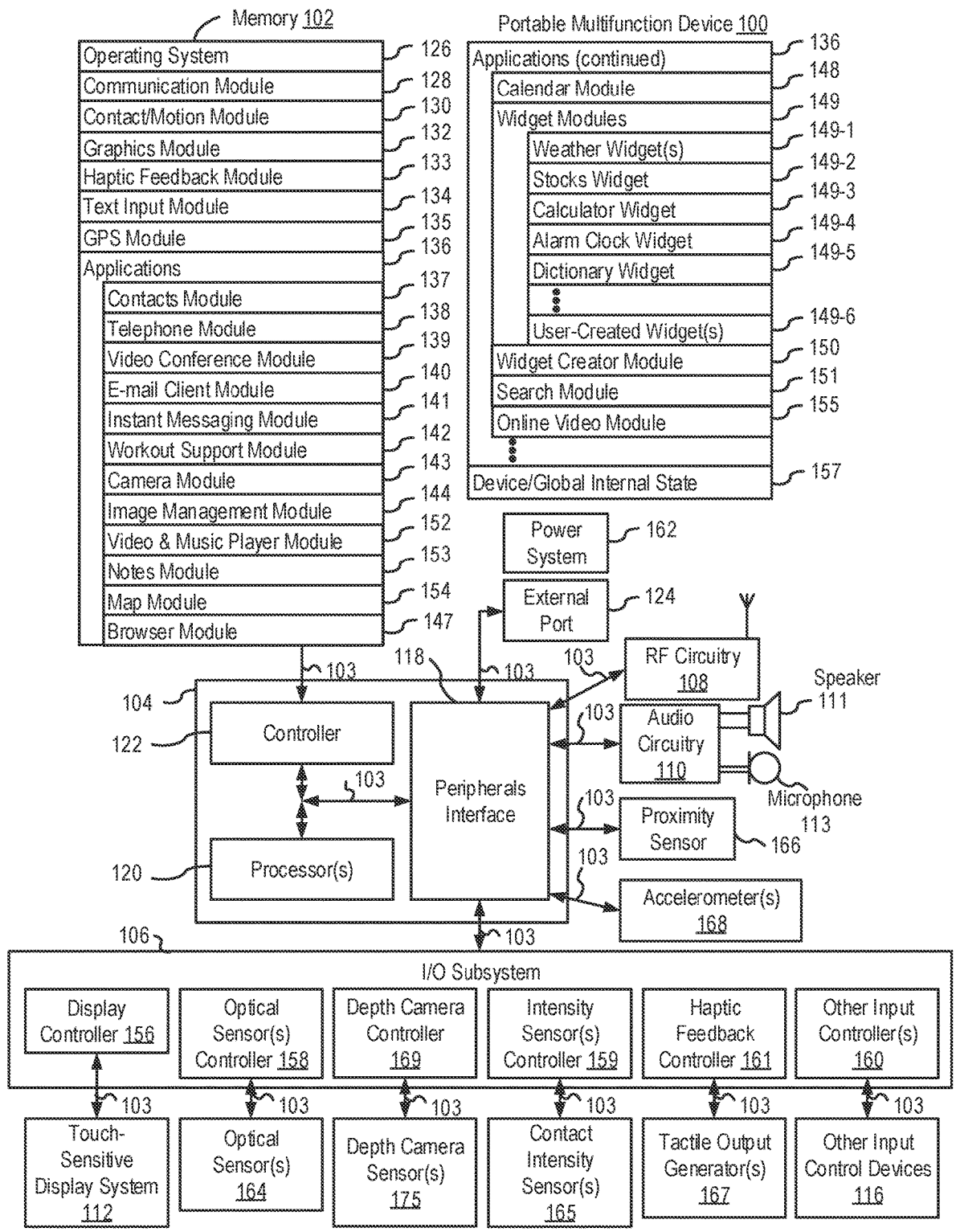
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (PO) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RE circuitry 108 converts electrical signals to/from electromagnetic signals and communicates with communications networks and other communications devices via the electromagnetic signals, RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NEC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, HSPA. (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VOW), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures and/or air gestures) as input. In some embodiments, the one or more input devices are integrated with the computer system. In some embodiments, the one or more input devices are separate from the computer system. In some embodiments, an air gesture is a gesture that is detected without the user touching an input element that is part of the device (or independently of an input element that is a part of the device) and is based on detected motion of a portion of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

A quick press of the push button optionally disengages a loch of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to de vice 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112, In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touch-screen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User interfaces For Touch Sensitive Input Devices," filed Jan. 18, 2005; (6) U.S. patent application Ser. No. 11/228,758, "Virtual Input Device Placement On A Touch Screen User interface," filed Sep. 16, 2005; (7) U.S. patent application Ser. No. 11/228, 700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Field Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing)) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a UPS (or GLONASS or other global navigation system) receiver for obtaining information concerning the location and orientation (e.g., portrait or landscape) of device 100.

Figure 3:
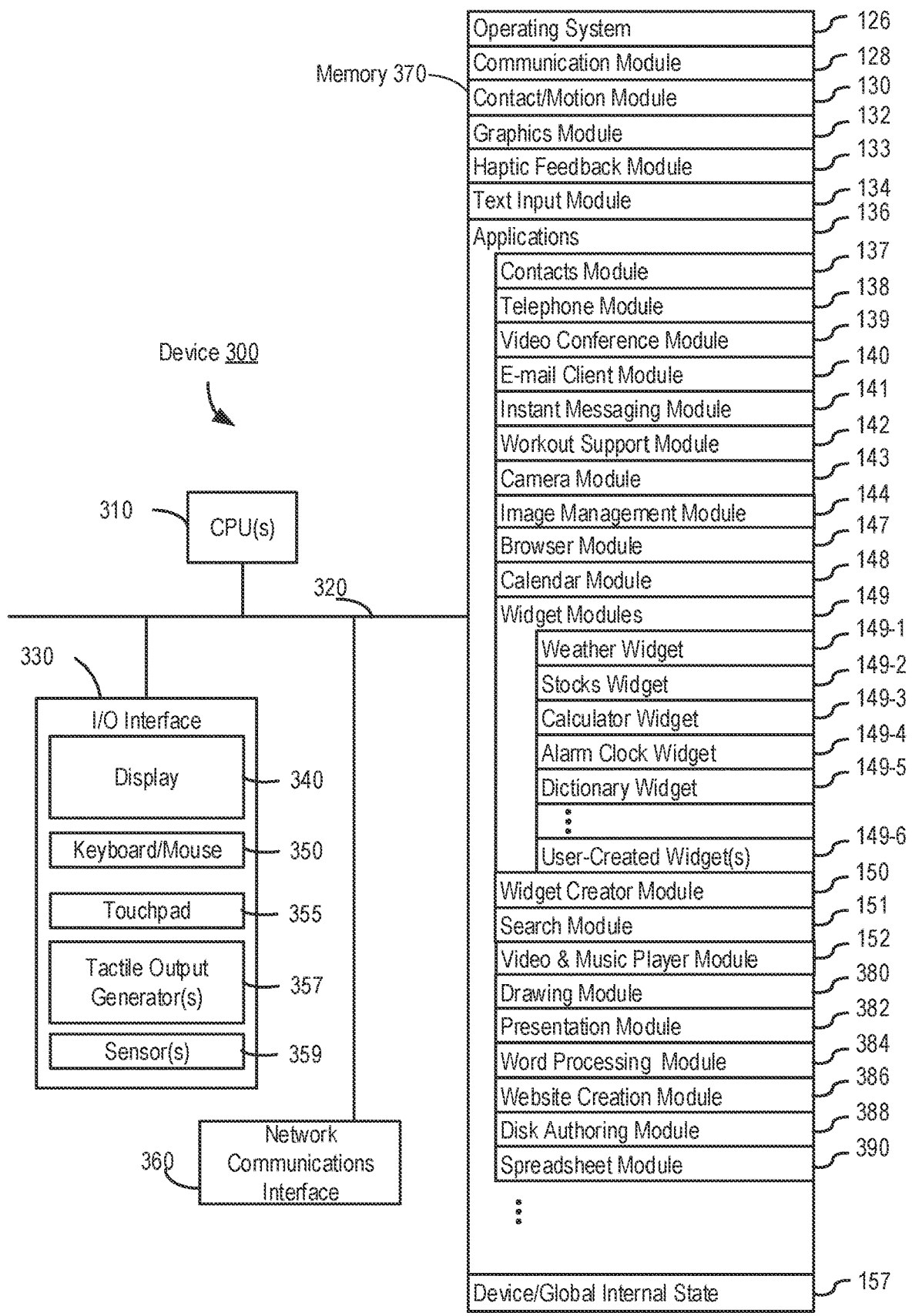
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (UPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124.

External port 124 (e.g., Universal Serial Bus (USB), FIRE-WIRE, etc) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across they touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used, Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 optionally include the following modules (or sets of instructions), or a subset or superset thereof:

- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or MIPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147 the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
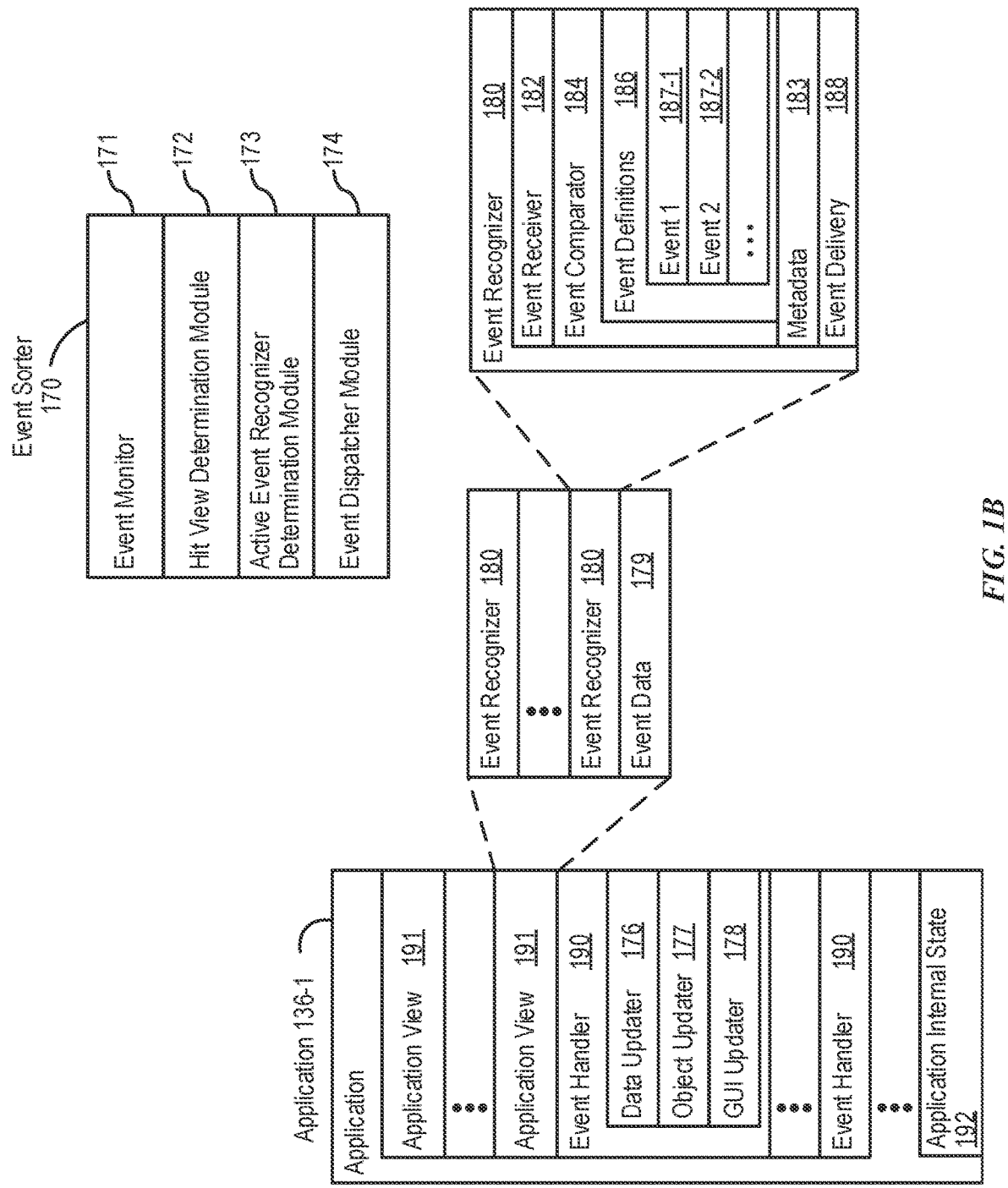
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118, Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170, Event handler 190 optionally utilizes or calls data updater 176, object updater 177, or CUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement, Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (87) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object, GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178, In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
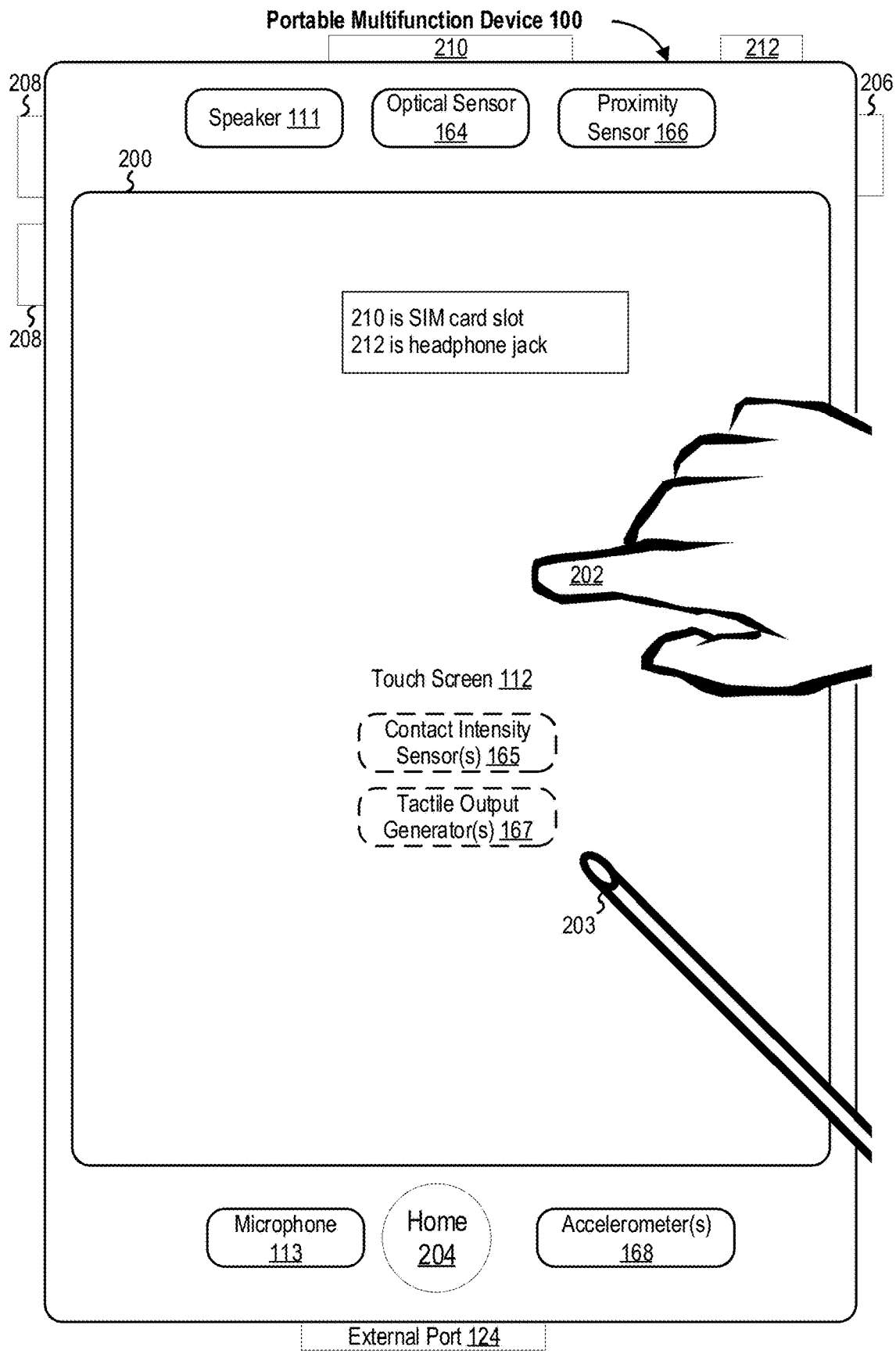
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113, Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
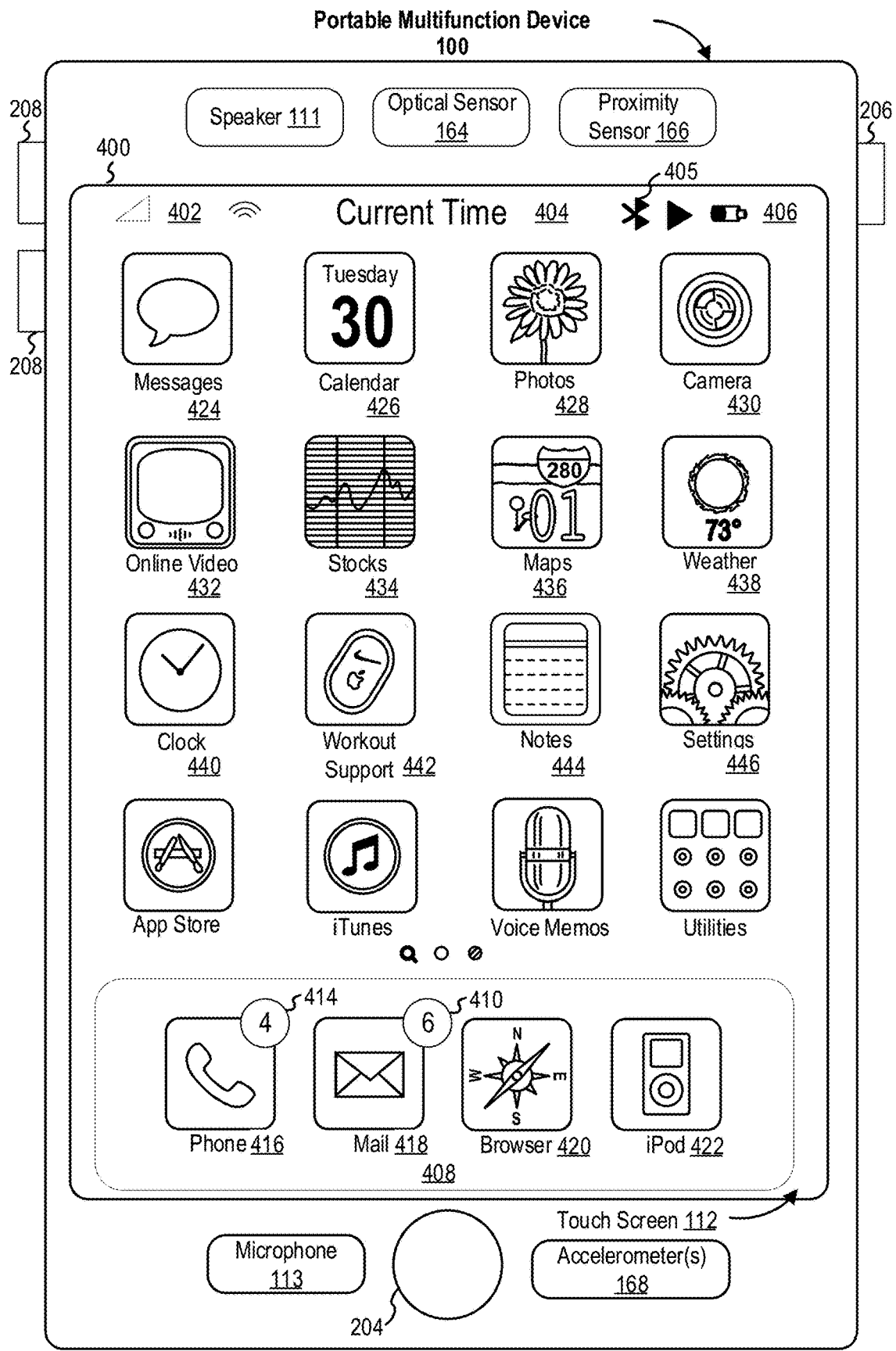
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments, Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;

Time 404;

Bluetooth indicator 405;

Battery status indicator 406;

Tray 408 with icons for frequently used applications, such as:

Icon 416 for telephone module 138, labeled "Phone," which optionally includes an indicator 414 of the number of missed calls or voicemail messages;

Icon 418 for e-mail client module 140, labeled "Mail," which optionally includes an indicator 410 of the number of unread e-mails, Icon 420 for browser module 147, labeled "Browser;" and Icon 422 for video and music player module 152, also referred to as iPod (trademark of Apple Inc.) module 152, labeled "iPod;" and Icons for other applications, such as:

Icon 424 for IM module 141, labeled "Messages;"

Icon 426 for calendar module 148, labeled "Calendar;"

Icon 428 for image management module 144, labeled "Photos;"

Icon 430 for camera module 143, labeled "Camera;"

Icon 432 for online video module 155, labeled "Online Video;"

Icon 434 for stocks widget 149-2, labeled "Stocks;"

Icon 436 for map module 154, labeled "Maps,"

Icon 438 for weather widget 149-1, labeled "Weather;"

Icon 440 for alarm clock widget 149-4, labeled "Clock,"

Icon 442 for workout support module 142, labeled "Workout Support;"

Icon 444 for notes module 153, labeled "Notes," and

Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
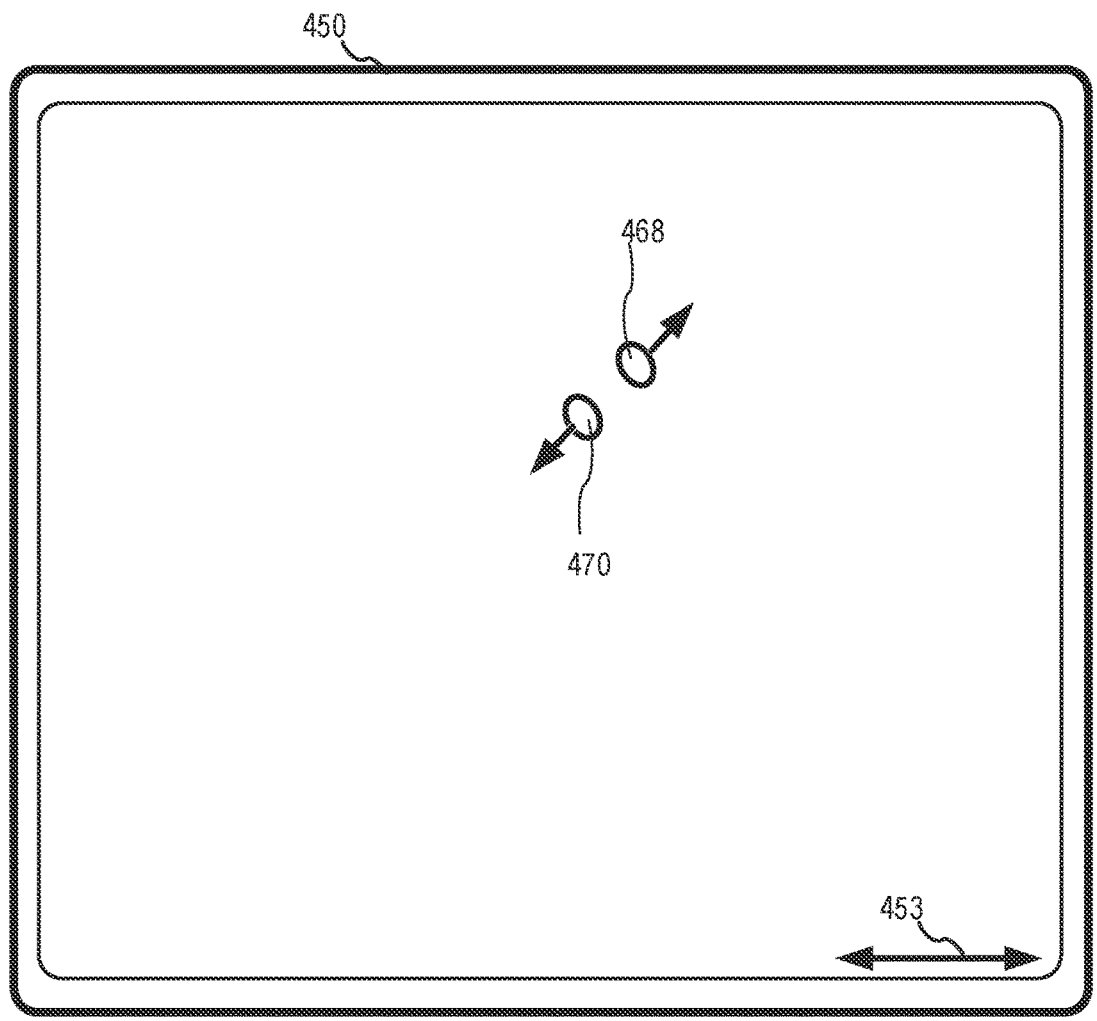
FIG. 4B illustrates an exemplary user interface for a multifunction device with a touch-sensitive surface that is separate from the display in accordance with some embodiments.
Figure 4B:
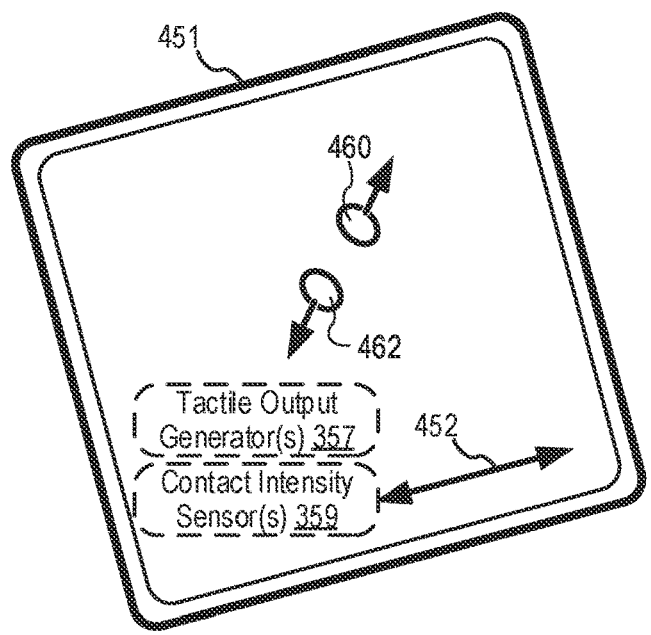

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
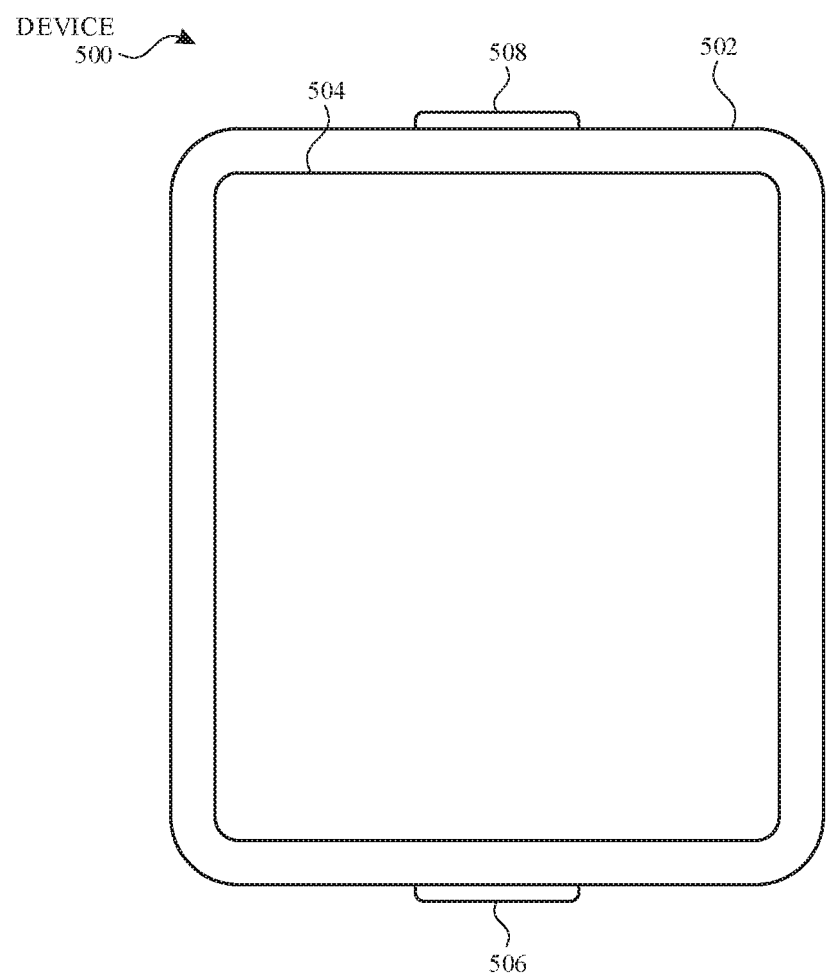
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504, Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
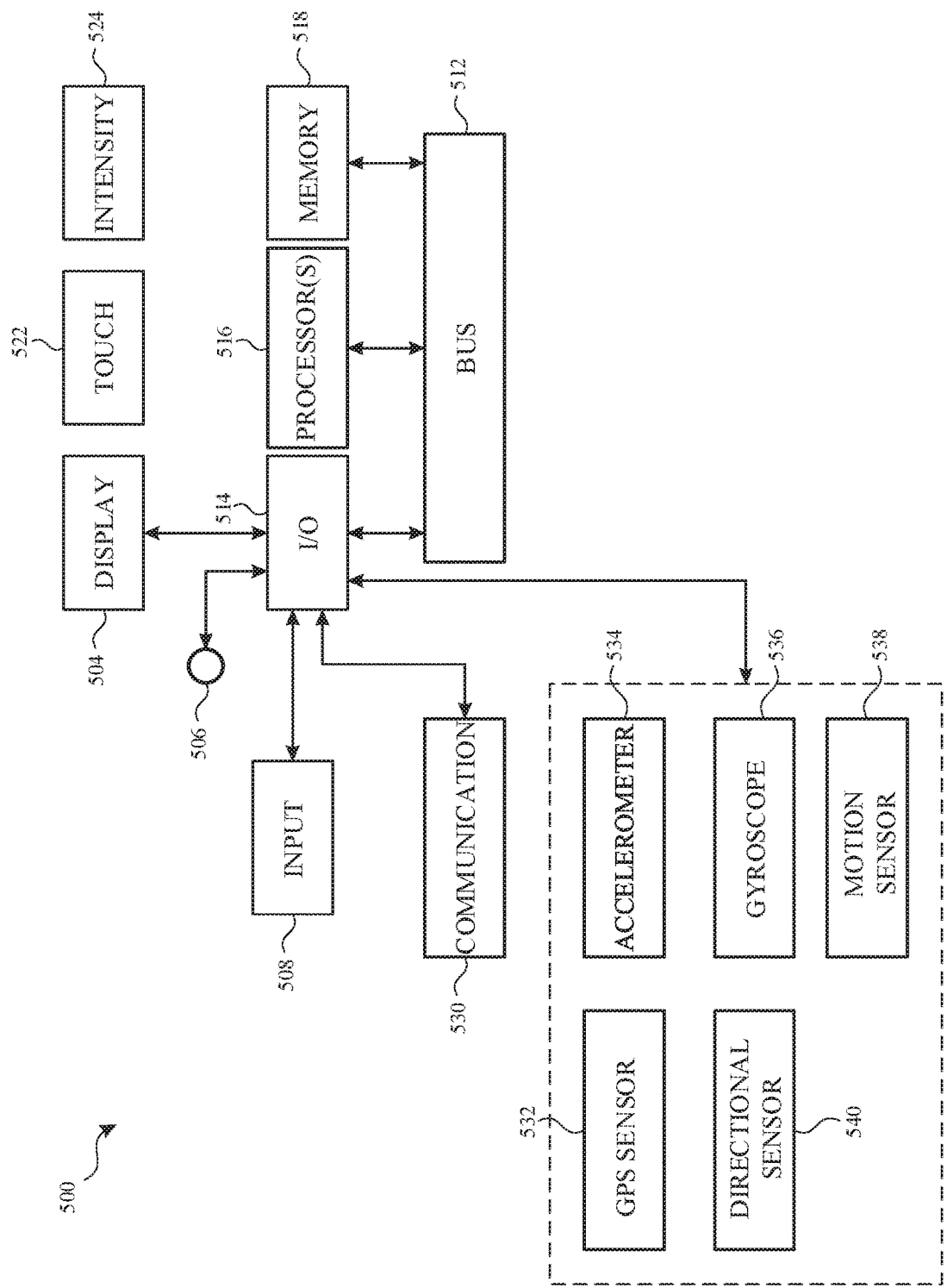
FIG. 5B is a block diagram illustrating a personal electronic device in accordance with some embodiments.

FIG. 5B depicts exemplary personal electronic device 500, In some embodiments, device 500 can include some or all of the components described with respect to FIGS. 1A, 113, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NEC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including process 700 (FIG. 7). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, EAT), or Blu-ray technologies, as well as persistent solid-state memory such as flash, solid-state drives, and the like, Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button) in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:
  an active application, which is currently displayed on a display screen of the device that the application is being used on;
  a background application (or background processes), which is not currently displayed, but one or more processes for the application are being processed by one or more processors; and
  a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6X illustrate exemplary user interfaces for recording the execution duration of functions, in accordance with some embodiments. The user interfaces in these figures are used to illustrate the processes described below, including the processes in FIG. 7.

FIG. 6A illustrates computer system 600 (e.g., an electronic device) displaying, via display 602, mindfulness user interface 620a, which includes audio meditation user-interactive graphical user interface object 608, reflect user-interactive graphical user interface object 610, and breathe user-interactive graphical user interface object 612. In some embodiments, computer system 600 optionally includes one or more features of device 100, device 300, or device 500. In some embodiments, computer system 600 is a tablet, phone, laptop, desktop, camera, etc. In some embodiments, the inputs described below can optionally be substituted for alternate inputs, such as a press input and/or a rotational input received via rotatable and depressible input mechanism 604.

Audio meditation user-interactive graphical user interface object 608, when selected, causes computer system 600 to initiate execution of an audio meditation function. Similarly, reflect user-interactive graphical user interface object 610, when selected, causes computer system 600 to initiate execution of a reflect function. Likewise, breathe user-interactive graphical user interface object 612, when selected, causes computer system 600 to initiate execution of a breathe function. In some embodiments, a selection corresponds to a tap input received on a corresponding user-interactive graphical user interface object.

Mindfulness user interface 620a includes user-interactive graphical user interface object 608, reflect user-interactive graphical user interface object 610, and breathe user-interactive graphical user interface object 612 displayed concurrently, such that execution of the audio meditations, the breathe function, and the reflect function can all be initiated from mindfulness user interface 620*a*. In some embodiments, mindfulness user interface 620*a* includes current time 606.

As illustrated in FIG. 6A, audio meditation user-interactive graphical user interface object 608 includes text 608*a* indicating that audio meditation user-interactive graphical user interface object 608 corresponds to an audio meditation function. Reflect user-interactive graphical user interface object 610 includes text 610*a* indicating that reflect user-interactive graphical user interface object 610 corresponds to a reflect function, duration indicator 610*b*, which indicates the currently selected duration for executing the reflect function, and additional information icon 610*c*, which, when selected, causes computer system 600 to display a user interface for viewing and/or for changing information related to the reflect function, such as the selected duration for executing the reflect function. Breathe user-interactive graphical user interface object 612 includes text 612*a* indicating that breathe user-interactive graphical user interface object 612 corresponds to a breathe function, duration indicator 612*b*, which indicates the currently selected duration for executing the reflect function, and additional information icon 612*c*, which, when selected, causes computer system 600 to display a user interface for viewing and/or changing information related to the breathe function, such as the selected duration for executing the breathe function.

At FIG. 6A, computer system 600 detects tap input 650*a* on audio meditation user-interactive graphical user interface object 608.

At FIG. 6B, in response to detecting tap input 650*a*, computer system 600 displays audio meditation options user interface 630*a*. Audio meditation options user interface 630*a* includes a plurality of user-interactive graphical user interface objects corresponding to audio meditations. Audio meditation options user interface 630*a* includes text 616 indicating that the plurality of user-interactive graphical user interface objects corresponding to audio meditations are new releases. In some embodiments, computer system 600 automatically (e.g., without user input) downloads newly released audio meditations (e.g., from a remote server). In some embodiments, computer system 600 automatically maintains the seven most recently released audio meditations, wherein each of the seven most recently released audio meditations corresponds to a different day of the week. In some embodiments, computer system 600 automatically deletes and/or purges old audio meditations when it downloads new ones, such that only the seven most recently released audio meditations are maintained (e.g., kept in local storage of computer system 600) by default. In some embodiments, the number of recently released audio meditations is not a fixed number but is, instead, equal to the number of mediations released within a predetermined period (e.g., the last week, two weeks, month).

At FIG. 6B, the plurality of user-interactive graphical user interface objects corresponding to audio meditations includes seven audio meditation user-interactive graphical user interface objects (614*a*, 614*b*, 614*c*, 614*d*, 614*e*, 614*f*, and 614*g*, respectively), including audio meditation user-interactive graphical user interface object 614*c*. Audio meditation user-interactive graphical user interface object 614*c* corresponds to an audio meditation titled "Compassion," as indicated by title 614*c*1. Audio meditation user-interactive graphical user interface object 614*c* includes instructor 614*c*2, which corresponds to the name of the instructor (speaker) delivering the audio meditation. At FIG. 6B, instructor 614*c*2 indicates that the instructor for the audio meditation corresponding to audio meditation user-interactive graphical user interface object 614*c* is Amy, Audio meditation user-interactive graphical user interface object 614*c* also includes duration 614*c*3, which at FIG. 6B indicates that the duration of the audio meditation corresponding to audio meditation user-interactive graphical user interface object 614*c* is 20 minutes. Audio meditation user-interactive graphical user interface object 614*c* further includes info 614*c*4, which, when selected, causes computer system 600 to display a user interface containing additional information about the audio meditation corresponding to audio meditation user-interactive graphical user interface object 614*c*.

Audio meditation options user interface 630*a* further includes back user-interactive graphical user interface object 617 which, when selected, causes computer system 600 to display the previously displayed user interface (e.g., mindfulness user interface 620*a*). Audio meditation options user interface 630*a* further includes current time 606. In some embodiments, the plurality of user-interactive graphical user interface objects corresponding to audio meditations (e.g., 614*a*, 614*b*, 614*c*, 614*d*, 615*e*, 614*f*, and 614*g*) each correspond to one or more of a limited number of categories. In some embodiments, the categories are "Renew," "Connect," and "Grow." in some embodiments, each audio meditation corresponds to only one category selected from the list of categories.

Audio meditation options user interface 630*a* further includes a library user-interactive graphical user interface object that, when selected, causes computer system 600 to display a user interface for viewing and/or for playing audio meditations stored in a library of audio meditations (e.g., a library of audio meditations that have been downloaded and/or saved in a library of computer system 600). In some embodiments, the audio meditations stored in the library of audio meditations are different from (e.g., in addition to) those represented by the audio meditations corresponding to the plurality of user-interactive graphical user interface objects (e.g., 614*a*, 614*b*, 614*c*, 614*d*, 615*e*, 614*f*, and 614*g*) in audio meditation options user interface 630*a*.

At FIG. 6B, computer system 600 detects tap input 650*b* on audio meditation user-interactive graphical user interface object 614*c*.

Figure 6C:
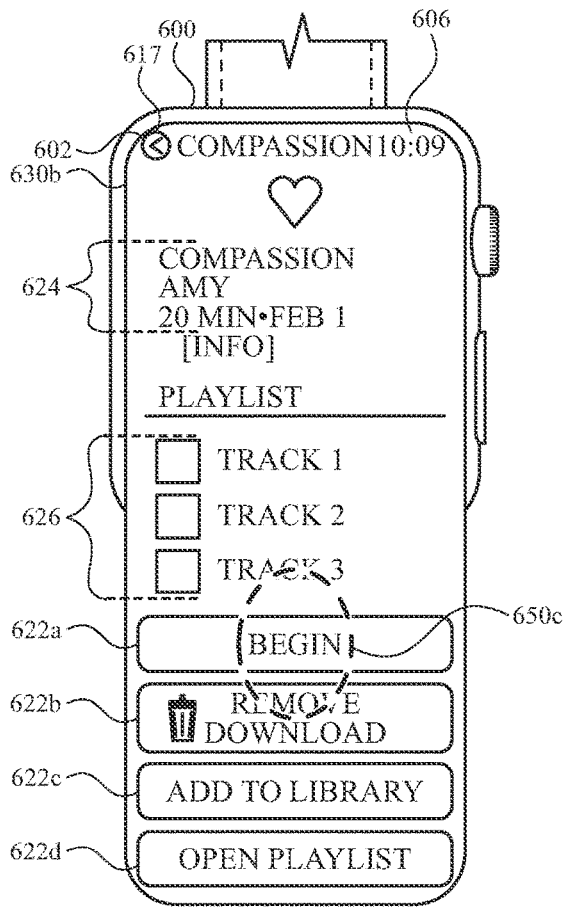

At FIG. 6C, in response to detecting tap input 650*b*, computer system 600 displays audio meditation options user interface 630*b*. Audio meditation options user interface 630*b* includes audio meditation info 624 that includes information related to the currently selected audio meditation, Audio meditation options user interface 630*b* further includes track info 626, which indicates a number of audio tracks related to the selected audio meditation and, in some embodiments, track titles related to the currently selected audio meditation, Audio meditation options user interface 630*b* includes begin user-interactive graphical user interface object 622*a* which, when selected, causes computer system 600 to begin playback of the selected audio meditation. Audio meditation options user interface 630*b* further includes remove download user-interactive graphical user interface object 622*b* which, when selected, causes computer system 600 to delete the selected audio meditation from computer system 600. Audio meditation options user interface 630*b* further includes add user-interactive graphical user interface object 622*c* which, when selected, causes computer system 600 to add the selected audio meditation 624 to a library of audio meditations. Audio meditation options user interface 630*b* includes open playlist user-interactive graphical user interface object 622*d* which, when selected, causes computer system 600 to display a playlist of media items related to (e.g., including) the currently selected audio meditation. Audio meditation options user interface 630*b* further includes back user-interactive graphical user interface object 617 and current time 606.

At FIG. 6C, computer system 600 detects tap input 650*c* on begin user-interactive graphical user interface object 622*a*.

Figure 6D:
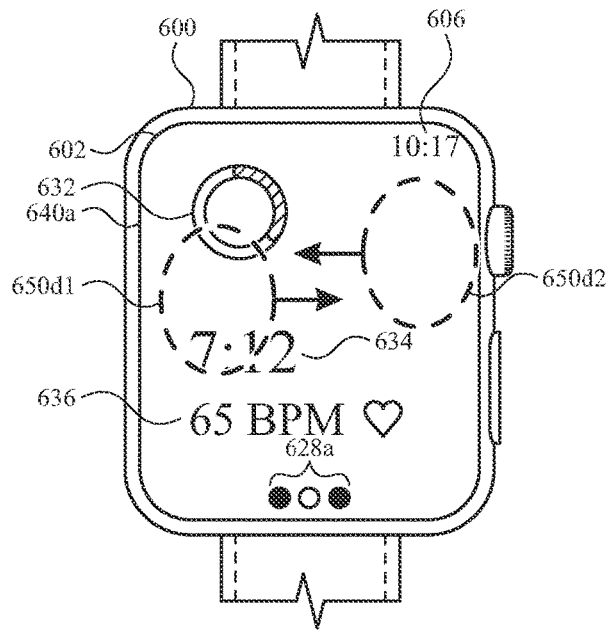

At FIG. 6D, in response to detecting tap input 650*c*, computer system 600 displays audio meditation playback user interface 640*a*. Audio meditation playback user interface 640*a* includes graphical representation 632. Graphical representation 632 is a visual representation depicting the elapsed playback time of the currently playing audio meditation relative to the total duration of the audio meditation. At FIG. 6D, graphical representation 632 is a ring that includes a first striped portion representing the portion of the currently playing audio meditation that has already played, and a second portion without stripes that represents the portion of the currently playing audio meditation that has not yet been played.

Audio meditation playback user interface 640*a* further includes elapsed time indicator 632. Elapsed time indicator represents the amount of time for which the currently executing audio meditation has been executing (e.g., playing). At FIG. 6D, elapsed time indicator 632 says 7:12, which indicates that the currently playing audio meditation has played for 7 minutes and 12 seconds.

Audio meditation playback user interface 640*a* further includes heart rate indicator 636. Heart rate indicator 636 represents a value of a physiological measurement currently being taken (e.g., by computer system 600). At FIG. 6D, heart rate indicator 636 says 65 BPM, which indicates that the heart rate of a user of computer system 600 is currently 65 beats per minute. In some embodiments, heart rate indicator 636 includes a graphical representation and/or textual indication of the type of measurement being indicated (e.g., a heart icon) and/or units of the measurements being conveyed (BPM). In some embodiments, heart rate indicator represents 636*a* value from a sensor that is integrated into and/or in communication with computer system 600 (e.g., a heart rate sensor). In some embodiments, heart rate indicator 636 is a substantially current value for a user utilizing (e.g., wearing) computer system 600.

Audio meditation playback user interface 640*a* further includes page indicator 628*a*. Page indicator 628*a* indicates the presence of additional user interfaces (e.g., pages) that a user can navigate to via swipe inputs on playback user interface 640*a*. Page indicator 628*a* indicates which of the available user interfaces (e.g., pages) is currently being displayed. At FIG. 6D, page indicator 628*a* indicates that there are three user interfaces (e.g., corresponding to the 3 dots). Page indicator 628*a* also indicates that audio meditation playback user interface 640*a* is in the middle of the three available user interfaces, because the middle dot is hollow whereas the two other dots are solid.

At FIG. 6D, computer system 600 detects swipe input 650*d*1 on audio meditation playback user interface 640*a* in a first direction, and swipe input 650*d*2 on audio meditation playback user interface 640*a* in a second direction different from the first direction.

Figure 6E:
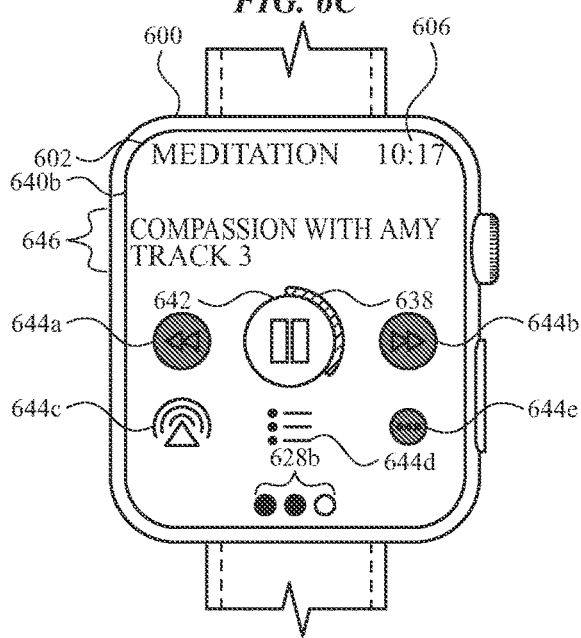

At FIG. 6E, in response to detecting swipe input 650*d*2, computer system 600 displays playback controls user interface 640*b*. Playback controls user interface 640*b* includes audio meditation info 646, which includes details about the currently executing audio meditation (e.g., the title, instructor, duration). Playback controls user interface 640*b* further includes playback controls 644*a* and 644*b*. At FIG. 6E, playback controls 644*a* and 644*b* are not able to be selected (e.g., are grayed out). In some embodiments, grayed out controls are not available and/or not applicable for the currently executing media (e.g., the currently executing audio meditation). Playback controls user interface 640*b* further includes playback control 644*c* which, when selected, causes computer system 600 to display options for playing the audio meditation via a particular device (e.g., via computer system 600, via a set of external speakers, via a set of headphones). Playback controls user interface 640*b* further includes playback control 644*d* which, when selected, causes computer system 600 to display a list of media items (e.g., audio meditations) that can be executed (e.g., played) via computer system 600. Playback controls user interface 640*b* further includes playback control 644*e*. At FIG. 6E, playback control 644*e* is grayed out, indicating that it is not applicable and/or is not available to be selected. In some embodiments, playback control 644*e*, when selected, causes computer system 600 to display additional information related to the currently executing audio meditation. Playback controls user interface 640*b* further includes page indicator 628*b*, which indicates that playback controls user interface 640*b* is the rightmost of three available user interfaces (pages).

Figure 6F:
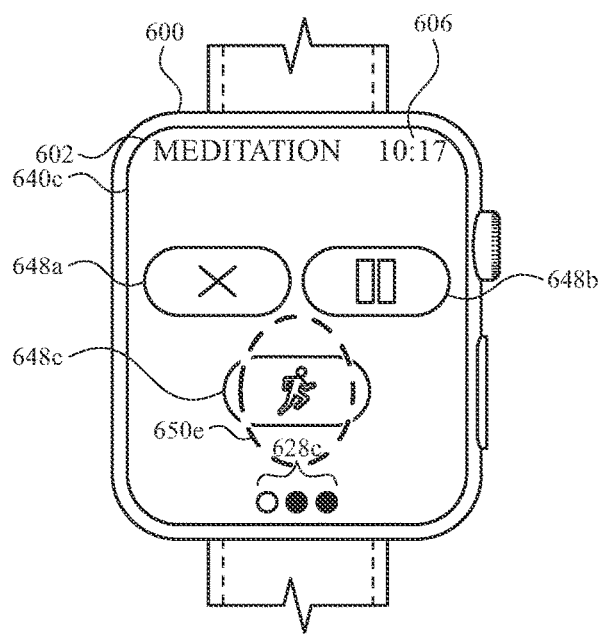

At FIG. 6F, in response to detecting swipe input 650*d*1, computer system 600 displays controls user interface 640*c*. Controls user interface 640*c* includes end user-interactive graphical user interface object 648*a* which, when selected, causes execution of the currently executing audio meditation to end. Controls user interface 640*c* further includes pause user-interactive graphical user interface object 648*b* which, when selected, causes the currently executing audio meditation to be paused (e.g., causes execution and/or playback to pause). Controls user interface 640*c* further includes workout user-interactive graphical user interface object 648*c* which, when selected, causes a workout user interface to be displayed. Controls user interface 640*c* further includes page indicator 628*c* which indicates that controls user interface 640*c* is the leftmost of three available user interfaces (pages).

At FIG. 6F, computer system 600 detects tap input 650*e* on workout user-interactive graphical user interface object 648*c*.

Figure 6G:
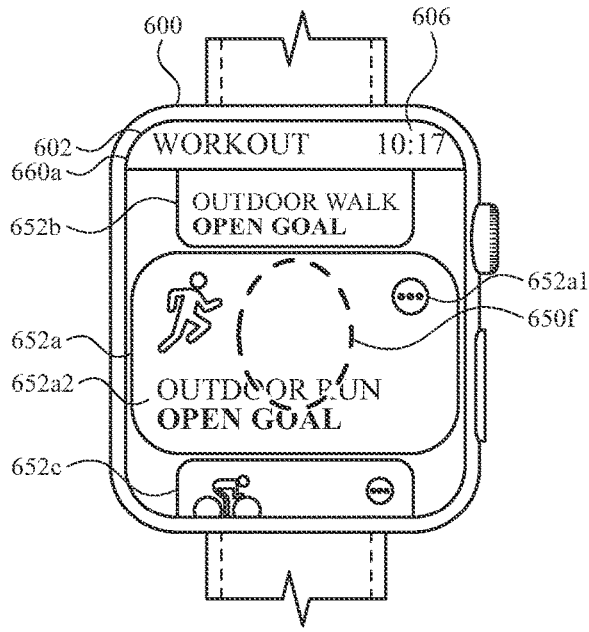

At FIG. 6G, in response to detecting tap input 650*e*, computer system 600 displays workout user interface 660*a*. In some embodiments, workout user interface 660*a* corresponds to a workout application different from the mindfulness application that corresponds to the user interfaces shown in FIGS. 6A-6F. Workout user interface 660*a* includes options for beginning workout functions, including walk user-interactive graphical user interface object 652*b*, which, when selected, causes computer system 600 to begin executing a walk tracking function. Workout user interface 660*a* further includes run user-interactive graphical user interface object 652*a* which, when selected, causes computer system 600 to begin executing a run tracking function. Workout user interface 660*a* further includes biking user-interactive graphical user interface object 652*c* which, when selected, causes computer system 600 to begin executing a bike tracking function.

At FIG. 6G, computer system 600 detects tap input 650*f* on run user-interactive graphical user interface object 652*a*. In response to detecting tap input 650*f*, computer system 600 begins executing a run tracking function while continuing to play the previously selected audio meditation concurrently.

Figure 6H:
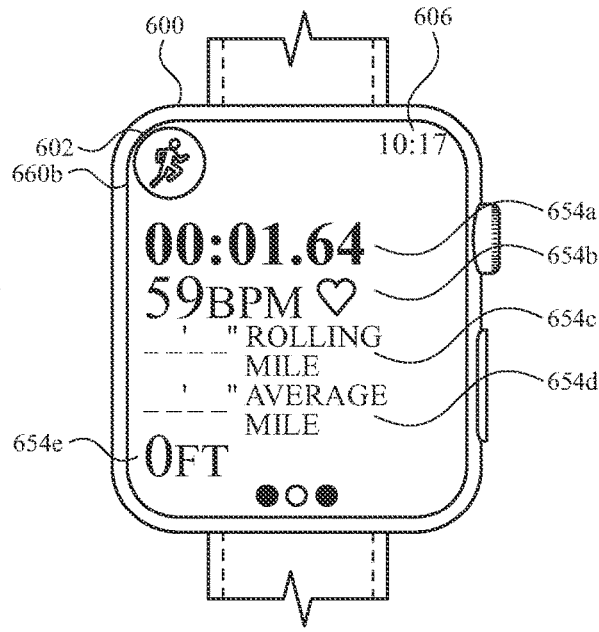

At FIG. 6H, in response to detecting tap input 650f, computer system 600 displays workout user interface 660b. Workout user interface 660b includes information for tracking a run, including: run time 654a, which indicates the amount of time that the run tracking function has been executing, heart rate 654b, which indicates a current heart rate measurement, rolling mile time 654c, which indicates a rolling mile time measured while the run tracking function has been executing, average mile time 654d, which indicates an average mile time measured while the run tracking function has been executing, and elevation 654e, which indicates the elevation while the run tracking function has been executing.

Figure 6I:
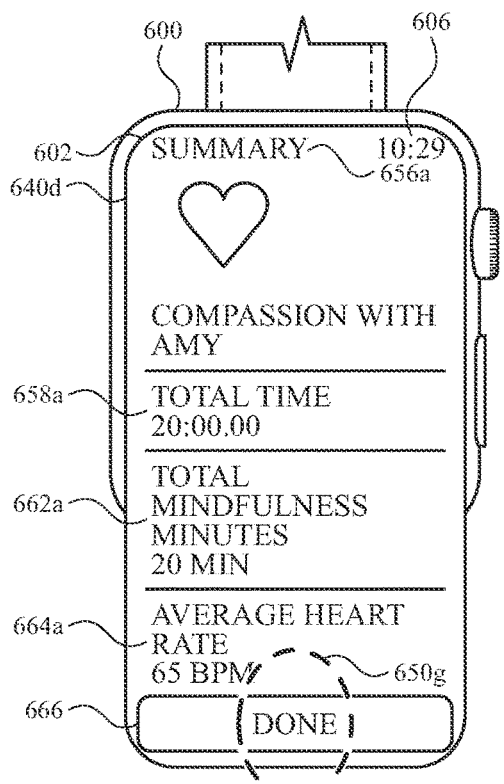

At FIG. 6I, after beginning to execute the run tracking function in FIG. 6G, computer system 600 determines that the audio meditation that continued playing while the run tracking function was executing has ended. Based on the determination that the audio meditation has ended, computer system 600 displays summary user interface 640d at FIG. 6I. In some embodiments, summary user interface 640d is provided by the same application that provided the user interfaces shown at FIGS. 6D-6F (user interfaces 640a, 640b, and 640c). Summary user interface 640e1 includes summary indicator 656a, which provides a textual and/or graphical indication that summary user interface 640d is a summary screen. Summary user interface 640d further includes function timer 658a, which indicates the total time spent executing the audio meditation, mindfulness minutes timer 662a, which indicates the total number of mindfulness minutes spent executing mindfulness functions executing audio meditations, executing a breathe function, executing a reflect function) within a threshold time period (e.g., within a day), heart rate 664a, which indicates the average heart rate measurement recorded during the audio meditation, and done user-interactive graphical user interface object 666 which, when selected, causes the computer system to display a user interface different from summary user interface 640d.

Function timer 658a indicates the number of minutes spent executing the audio meditation within a time range. At FIG. 6I, function timer 658a indicates that the audio meditation has executed for 20 minutes within the time range, Mindfulness minutes timer 662a indicates the cumulative number of minutes that mindfulness functions have executed during the time range. In the embodiment of FIGS. 6A-6X, mindfulness functions include audio meditations, the breathe function, and the reflect function, but do not include certain other functions, such as the run tracking function of workout user interface 660b. Thus, mindfulness minutes timer 662a includes the number of minutes that audio meditations have played and the number of minutes that the breathe function and the reflect function have executed within the time range (e.g., within the current day). At FIG. 6I, mindfulness minutes timer 662a indicates that mindfulness activities have executed for 20 minutes within the time range. Function timer 658a indicates that the audio meditation function has executed for 20 minutes within the time range. So, at FIG. 6I, all of the mindfulness minutes indicated by mindfulness minutes timer 662a conic from the execution of the audio meditation that has just ended, indicating that this is the total amount of time that qualifying mindfulness functions were executed in the time range. At FIG. 6I, summary user interface 640d includes current time 606, wherein the current time is now updated to reflect that 20 minutes (the duration of the audio meditation) have passed since the audio meditation was started at FIG. 6C.

After beginning to execute the run tracking function in FIG. 6G, computer system 600 determines that the run tracking function has ended. In some embodiments, the run tracking function ends in response to a sequence of one or more inputs received by computer system 600. In some embodiments, the run tracking function ends after a predetermined amount of time. In some embodiments, the workout tracking functions ends in response to a determination that an activity level has fallen below a threshold level for a threshold duration of time.

Figure 6J:
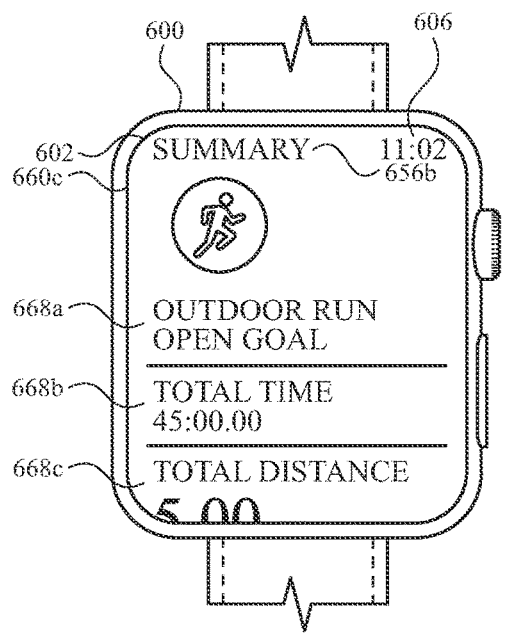

At FIG. 6J, in response to the run tracking function ending, computer system 600 displays workout summary user interface 660c. In some embodiments, workout summary user interface 660c is provided by the same application that provided the workout user interfaces shown at FIGS. 6G-6H (user interfaces 660a, 660b). Workout summary user interface 660c includes summary indicator 656b, which provides a textual and/or graphical indication that summary user interface 660c is a summary screen. Summary user interface 660c further includes run tracking information including run info 668a, which indicates the type of run (e.g., outdoor, open goal), run time 668b, which indicates the total time for which the run tracking function was executing, and distance 668c, which indicates the measured distance that was run while the run tracking function was executing. At FIG. 6J, workout summary user interface 660c further includes current time 606, wherein the current time is now updated to reflect that 45 minutes (the duration of the run) have passed since the run tracking function was started at FIG. 6G. Notably, the additional time that the run tracking function executed (e.g., from 10:29 until 11:02) is not added to mindfulness minutes timer 662a because the run tracking function is not a mindfulness function. Thus, the audio meditation function and the run tracking function executed concurrently, and different timers captured the execution time of each function.

At FIG. 6I, computer system 600 detects tap input 650g on done user-interactive graphical user interface object 666. In some embodiments, in response to detecting selection of done user-interactive graphical user interface object 666, computer system 600 dismisses summary user interface 640d and displays the user interface that was being displayed prior to summary user interface 640d being displayed. In some embodiments, in response to selection of done user-interactive graphical user interface object 666, computer system 600 displays mindfulness user interface 620a.

Figure 6K:
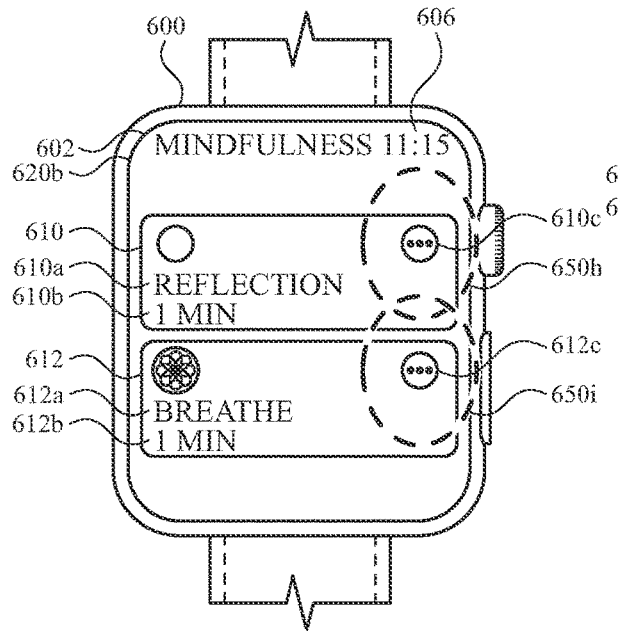

At FIG. 6K, in response to detecting tap input 650g, computer system 600 displays mindfulness user interface 620b. Mindfulness user interface 620b includes reflect user-interactive graphical user interface object 610, and breathe user-interactive graphical user interface object 612 without displaying audio meditation user-interactive graphical user interface object 608, Displaying reflect user-interactive graphical user interface object 610, and breathe user-interactive graphical user interface object 612 without displaying audio meditation user-interactive graphical user interface object 608 in response to detecting selection of done user-interactive graphical user interface object 666 in the summary screen after an audio meditation has ended allows a second mindfulness experience (breathe, reflect) to be quickly and efficiently started after an audio meditation has ended with few user inputs, thereby enabling a user to quickly and efficiently start a second function that shares a timer with the ended audio meditation function (e.g., the mindfulness minutes timer).

At FIG. 6K, computer system 600 detects tap input 650*h* on additional information icon 610*c* and tap input 650*i* on additional information icon 612*c*. In some embodiments, computer system 600 receives a tap input on reflect user-interactive graphical user interface object 610 and, in response to receiving the tap input, initiates execution of the reflect function. In some embodiments, computer system receives a tap input on breathe user-interactive graphical user interface object 612 and, in response to receiving the tap input, initiates execution of the breathe function.

Figure 6L:
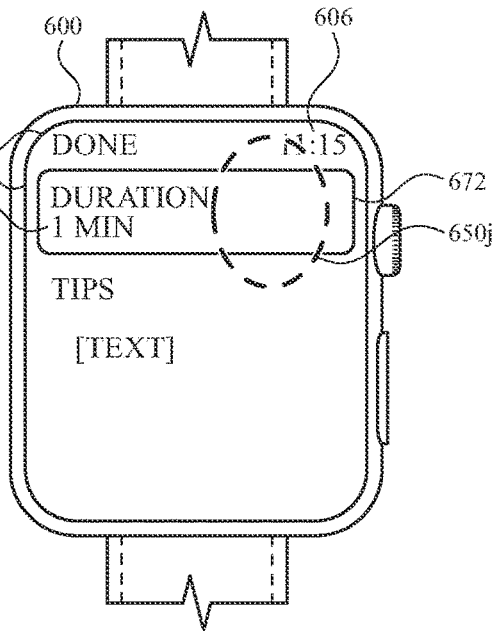

At FIG. 6L, in response to receiving tap input 650*h* or 650*i*, computer system 600 displays options user interface 670*a*. Duration options user interface 670*a* includes information about the options currently selected for executing a selected function. In response to detecting tap input 650*h*, computer system 600 displays options user interface 670*a* with options for executing the reflect function. In response to detecting tap input 650*i*, computer system 600 displays options user interface 670*a* with options for executing the breathe function. At FIG. 6L, options user interface 670*a* includes duration user-interactive graphical user interface object 672 which, when selected, causes computer 600 to display duration options for executing the selected function. At FIG. 6L, duration user-interactive graphical user interface object 672 includes current duration indicator 672*a*, which indicates that the currently selected duration for executing the selected function is one minute. In some embodiments, options user interface 670*a* further includes a start user-interactive graphical user interface object that, when selected, causes computer system 600 to begin executing the selected function for the selected duration indicated by current duration indicator 672*a*.

At FIG. 6L, computer system 600 detects tap input 650*j* on duration user-inte ac graphical user interface object 672.

Figure 6M:
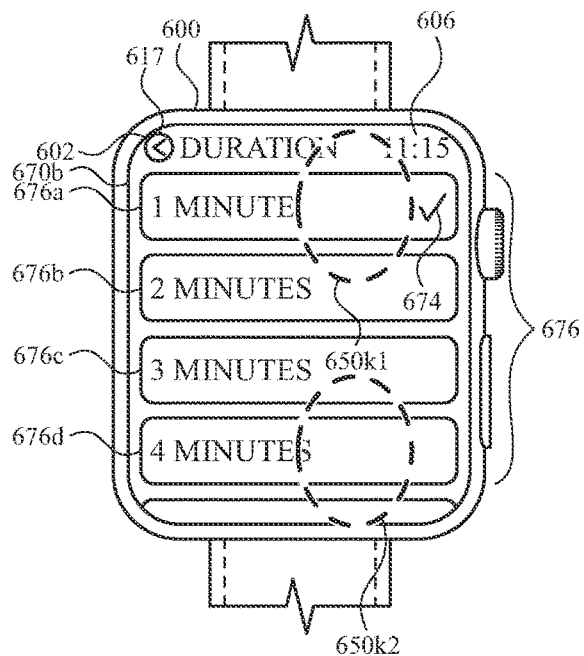

At FIG. 6M, in response to receiving tap input 650*j*, computer system 600 displays options user interface 670*b*. Options user interface 650*b* includes minute indicators that correspond to different minute duration options. In particular, minute indicator 676*a* corresponds to an option for executing a function for 1 minute, minute indicator 676*b* corresponds to an option for executing a function for 2 minutes, minute indicator 676*c* corresponds to an option for executing a function for 3 minutes, and minute indicator 676*d* corresponds to an option for executing a function for 4 minutes. In some embodiments, options user interface 670*b* includes different time increments or duration options. Options user interface 670*b* further includes selection indicator 674, which indicates the currently selected minute indicator (e.g., 676*a*, 676*b*, 676*c*, 676*d*). At FIG. 6M, selection indicator 674 is a checkmark indicating that the currently selected duration is 1 minute. Options user interface 670*b* further includes back user-interactive graphical user interface object 617 and current time 606. In some embodiments, options user interface further includes a start user-interactive graphical user interface object that, when selected, causes computer system 600 to begin executing the selected function for the selected duration. In some embodiments, detecting a tap on the currently selected duration causes computer system 600 to initiate execution of the selected function for the selected duration.

At FIG. 6M, computer system 600 detects tap input 650*k*1 on minute indicator 676*a* and tap input 650*k*2 on minute indicator 676*d*.

Figure 6N:
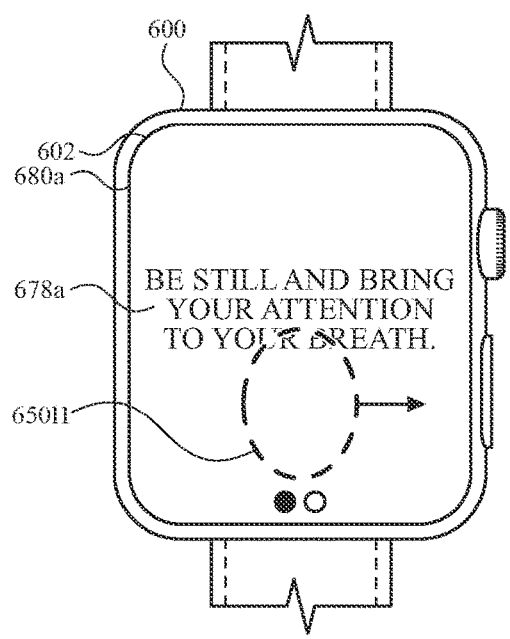

At FIG. 6N, in response to receiving tap input 650*k*1 after the breathe function has been selected (e.g., via tap input 650*i* at FIG. 6K), computer system 600 displays breathe user interface 680*a*. Displaying breathe user interface 680*a* corresponds to executing a breathe function. Breathe user interface 680*a* includes breathe graphic 678*a*, which includes text related to the breathe function. In some embodiments, breathe user interface 678*a* is displayed in response to a tap input received on breathe user-interactive graphical user interface object 612 at FIG. 6A and/or at FIG. 6K.

Breathe user interface 680*a*, 680*b*, and 680*c* further include page indicator 628*d*, which indicates the presence of additional user interfaces (e.g., pages) that a user can swipe over to from the currently displayed user interface, and indicates which of the available user interfaces (pages) is currently being displayed. At FIGS. 6N, 6O, and 6P, page indicator 628*d* indicates that there are two user interfaces (e.g., 2 dots), and that breathing user interfaces 680*a*, 680*b*, and 680*c* are the rightmost user interface of the two available user interfaces (pages).

Breathe user interface 680*a* does not include back user-interactive graphical user interface object 617 or current time 606. Displaying breathe user interface 680*a* without displaying back user-interactive graphical user interface object 617 or current time 606 minimizes extraneous information included in the user interface and encourages the user to focus on the elements of breathe user interface 680*a* without being distracted by back user-interactive graphical user interface object 617 or current time 606. In particular, displaying breathe user interface 680*a* without displaying current time 606 simplifies the user interface, presents the breathe function in a clear, uncluttered way, encourages a user to be focused and mindful, and limits visual distraction. The above description of displaying breathe user interfaces without back user-interactive graphical user interface object 617 or current time 606 also applies to breathe user interface 680*b* and breathe user interface 680*c*, which are discussed below.

At FIG. 6N, computer system 600 detects swipe input 650/1 on breathe user interface 680*a*. In response to detecting swipe input 650/1, computer system 600 displays end user interface 682*c*, which is discussed below with regard to FIG. 6T. In some embodiments, a swipe input is received while breathe user interface 680*b* or 680*c* is displayed (e.g., at FIG. 6O or 6P) and, in response to receiving the swipe input, computer system 600 displays end user interface 682*c*.

Computer system 600 displays information related to the breathe function while the breathe function is executing. At FIG. 6O, after displaying breathe user interface 680*a*, and while executing the breathe function, computer system 600 displays breathe user interface 680*b* which includes graphical object 678*b*. Graphical object 678*b* includes text and/or a graphical indication of a user's breath. In some embodiments, portions of graphical object 678*b* are animated to shrink and expand in sequence (e.g., rhythmically) to a current and/or recommended breath pattern.

Figure 6O:
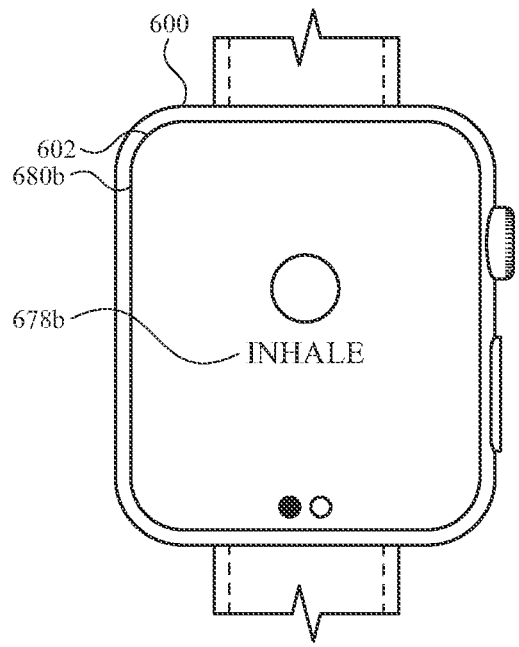
Figure 6P:
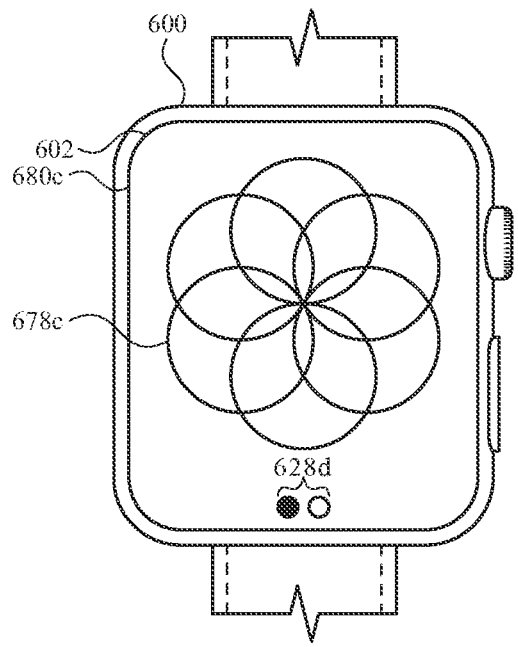

At FIG. 6P, after displaying breathe user interface 680*b*, while executing the breathe function, computer system 600 displays breathe user interface 680*c* which includes graphical object 678*c*, Graphical object 678*c* includes a graphical indication of breath. In some embodiments, graphical object 678*c* is animated to shrink and expand in sequence (e.g., rhythmically) to a current or recommended breath pattern. In some embodiments, the order in which user interfaces 680*a*, 680*b*, and 680*c* are displayed is interchangeable. In some embodiments, computer system cycles through displaying breathe user interfaces 680*a*, 680*b*, and 680*c* while the breathe function is executing (e.g., multiple times). In some embodiments, the order in which user interfaces 680a, 680b, and 680c are displayed changes while the breathe function executes.

Figure 6Q:
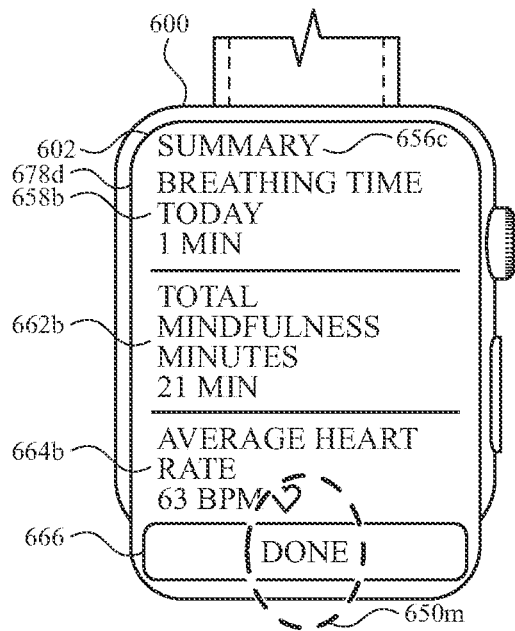

After executing the breathe function in FIGS. 6N-6P, computer system 600 determines that the breathe function has ended (e.g., the selected duration has expired), and displays summary user interface 678d. At FIG. 6Q, summary user interface 678d includes summary indicator 656c, which provides a textual and/or graphical indication that summary user interface 678d is a summary screen. Summary user interface 678d further includes function timer 658b, which indicates the number of minutes that the breathe function has executed during a time range (e.g., during the current day). Summary user interface 640d further includes mindfulness minutes timer 662b, which indicates the total number of mindfulness minutes spent executing mindfulness functions (e.g., executing audio meditations, executing a breathe function, executing a reflect function), including the breathe function, within a threshold time period (e.g., during the current day), heart rate 664b, which indicates the average heart rate measurement recorded while the breathe function was executing, and done user-interactive graphical user interface object 666 which, when selected, causes the computer system to display a user interface different from summary user interface 678d.

Function timer 658b indicates the number of minutes spent executing the breathe function within a current time range. At FIG. 6Q, function timer 658b indicates that the breathe function has executed for 1 minute within the current day. Mindfulness minutes timer 662b indicates the cumulative number of minutes that mindfulness functions have executed during the time range. (e.g., within the current day) At FIG. 6Q, mindfulness minutes timer 662b indicates that mindfulness activities have executed for 21 minutes within the time range. Function timer 658b indicates that the breathe function has executed for 1 minute within the time range. So, at FIG. GQ, the mindfulness minutes indicated by mindfulness minutes timer 662b come from both the 1 minute spent executing the breathe function and the prior 20 minutes spent executing the audio meditation (as previously discussed in relation to FIG. 6I). Notably, however, the mindfulness minutes timer does not include the additional time spent executing functions that are not considered mindfulness functions, such as the run tracking function that executed for 45 minutes (as discussed in relation to FIG. 6J).

Figure 6R:
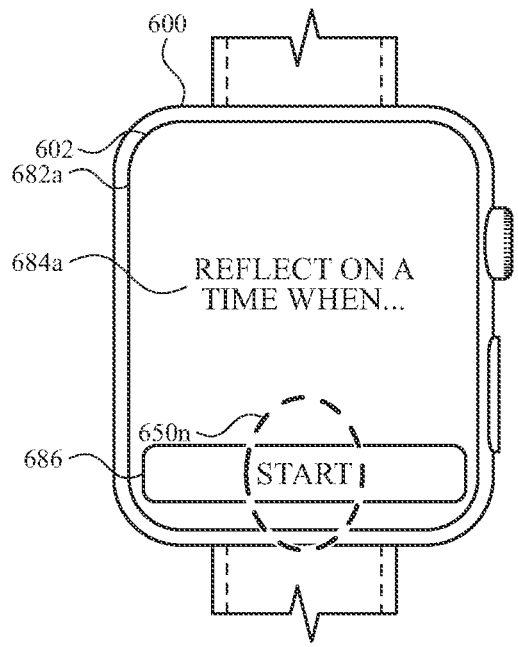

In FIG. 6R, in response to receiving tap input 650k2 at FIG. 6M after the reflect function has been selected (e.g., via tap input 650h at FIG. 6K), computer system 600 displays reflect user interface 682a. Reflect user interface 682a includes reflect prompt 684a, which includes text related to the reflect function. In some embodiments, reflect user interface 682a is displayed in response to a tap input received on reflect user-interactive graphical user interface object 610 at FIG. 6A and/or at FIG. 6K, Reflect user interface 682a further includes start user-interactive graphical user interface object 686 which, when selected, causes computer system 600 to execute the reflect function.

In some embodiments, reflect prompt 684a includes a textual statement prompting the user to reflect on a certain topic. In some embodiments, the textual statement is randomly selected from a predefined list of possible topics. In some embodiment, the possible prompts for phrases to be included in reflect prompt 684a are from correspond to one or more of a limited number of categories. In some embodiments, the categories are "Renew," "Connect," and "Grow,"

In some embodiments, each phrase included in reflect prompt 684a corresponds to only one category selected from the list of categories.

At FIG. 6R, computer system 600 detects tap input 650n on start user-interactive graphical user interface object 686.

Figure 6S:
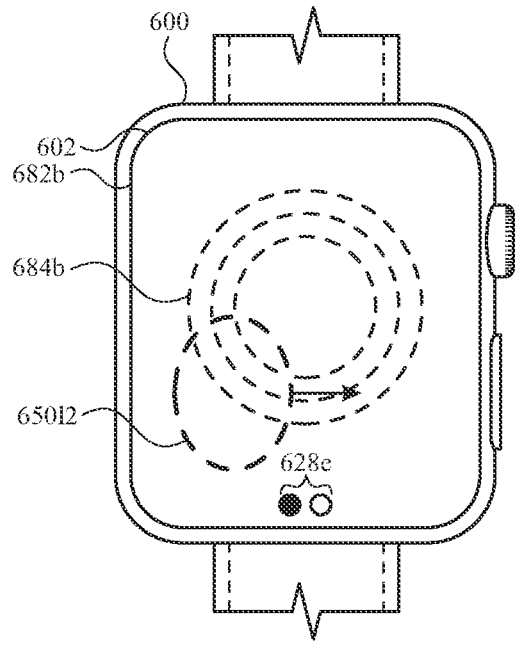

At FIG. 6S, in response to detecting tap input 650n, computer system 600 displays reflect user interface 682b, which includes graphical object 684b. Graphical object 654b corresponds to a graphical visualization corresponding to the reflect function.

Reflect user interface 682b further includes page indicator 628e, which indicates the presence of additional user interfaces (e.g., pages) that a user can swipe over to from the currently displayed user interface, and indicates which of the available user interfaces (pages) is currently being displayed. At FIG. 6S, page indicator 628e indicates that there are two user interfaces (e.g., 2 dots), and that reflect user interface 682b is the rightmost user interface of the two available user interfaces (pages).

Reflect user interface 682b does not include back user-interactive graphical user interface object 617 or current time 606. Displaying reflect user interface 682b without displaying back user-interactive graphical user interface object 617 or current time 606 minimizes extraneous information included in the user interface and encourages the user to focus on the elements of reflect user interface 682b without being distracted by back user-interactive graphical user interface object 617 or current time 606. In particular, displaying reflect user interface 682b without displaying current time 606 simplifies the user interface, presents the reflect function in an uncluttered way, brings focus and emphasis to reflect prompt 684a, and limits visual distractions.

At FIG. 6S, computer system 600 detects swipe input 650/2 on reflect user interface 682b. In response to detecting swipe input 650/2, computer system 600 displays end user interface 682c. End user interface includes end user-interactive graphical user interface object 688 which, when selected, causes the currently executing mindfulness function (e.g., breathe or reflect, depending on which function is currently executing) to stop executing (e.g., before the previously selected duration for execution has expired), In some embodiments, the mindfulness function stops executing in response to a tap input on end user-interactive graphical user interface object 688. End user interface 682c further includes page indicator 628f. At FIG. 6T, page indicator 628f indicates that there are two user interfaces (e.g., 2 dots), and that end user interface 682c is the leftmost user interface of the two available user interfaces (pages), In some embodiments, in response receiving a swipe input while end user interface 682c is displayed, computer system 600 displays a user interface corresponding to the currently executing mindfulness function (e.g., 680a, 680b, 680c, 682b).

Figure 6T:
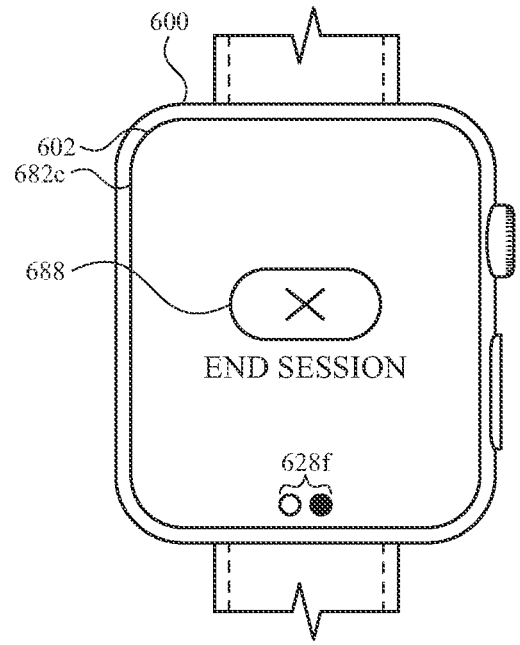
Figure 6U:
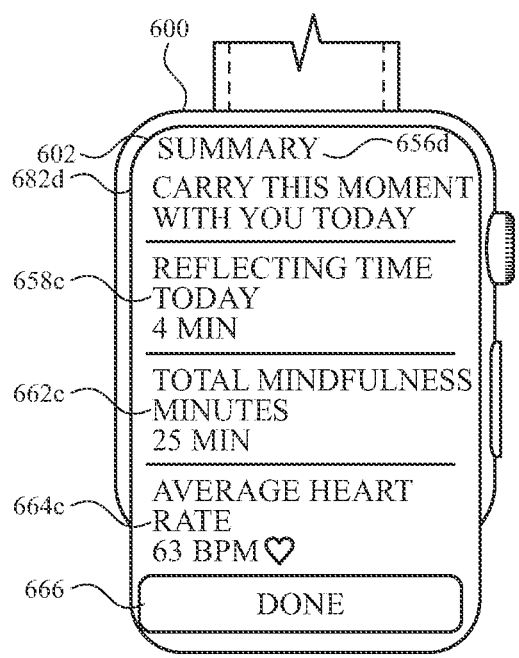

After executing the reflect function in FIGS. 6S-6T, computer system 600 determines that the reflect function has ended (e.g., the selected duration has expired), and displays summary user interface 682d. At FIG. 6U, summary user interface 682d includes summary indicator 656d, which provides a textual and/or graphical indication that summary user interface 682d is a summary screen. Summary user interface 682d further includes function timer 658c, which indicates the number of minutes that the reflected function has executed during a time range (e.g., during the current day). Summary user interface 682d further includes mindfulness minutes timer 662c, which indicates the total number of mindfulness minutes spent executing mindfulness functions (e.g., executing audio meditations, executing a breathe function, executing a reflect function), including the reflect function, within a threshold time period (e.g., during the current day), heart rate 664c, which indicates the average heart rate measurement recorded while the reflect function was executing, and done user-interactive graphical user interface object 666 which, when selected, causes the computer system to display a user interface different from summary user interface 678d.

Function timer 658c indicates the number of minutes spent executing the reflect function within a current time range. At FIG. 6U, function timer 658c indicates that the reflect function has executed for 4 minutes within the current day. Mindfulness minutes timer 662c indicates the cumulative number of minutes that mindfulness functions have executed during the time range. Mindfulness minutes timer 662c includes the number of minutes that audio meditations have executed, the number of minutes that the breathe function has executed, and, now, the number of minutes that the reflect function has executed within the time range (e.g., within the current day). At FIG. 6U, mindfulness minutes timer 662c indicates that mindfulness activities have executed for 25 minutes within the time range. Function timer 658c indicates that the reflect function has executed for 4 minutes within the time range, so, at FIG. 6U, the mindfulness minutes indicated by mindfulness minutes tinier 662c are from the 4 minutes spent executing the reflect function, the 1 minute spent executing the breathe function (as previously discussed in relation to FIG. 6Q), and the 20 minutes spent executing the audio meditation (as previously discussed in relation to FIG. 6I). Notably, however, the mindfulness minutes timer does not include the additional time spent executing functions that are not considered mindfulness functions, such as the run tracking function that executed for 45 minutes (as discussed in relation to FIG. 6I).

Figure 6V:
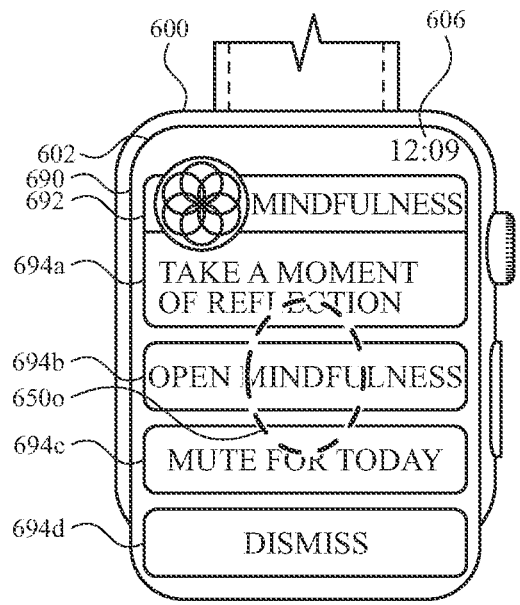

At FIG. 6V, computer system 600 displays notification user interface 690 in response to receiving and/or generating a notification related to the mindfulness application. Notification user interface 690 includes prompt 694a, which includes text and/or images related to the mindfulness application. Notification user interface 690 further includes open user-interactive graphical user interface object 694b which, when selected, causes computer system 600 to open (e.g., launch) the mindfulness application. In some embodiments, in response to receiving a tap input on open user-interactive graphical user interface object 694b, computer system 600 displays mindfulness user interface 620a. Notification user interface 690 further includes mute user-interactive graphical user interface object 694c which, when selected, causes additional notifications related to the mindfulness application to be muted (e.g., suppressed) for a time range. In some embodiments, in response to receiving selection of the mute user-interactive graphical user interface object 694c, computer system 600 suppresses notifications related to the mindfulness application by foregoing displaying notification user interfaces about the mindfulness application for a time period (e.g., 1 day). Notification user interface 690 further includes dismiss user-interactive graphical user interface object 694d which, when selected, causes computer system to cease displaying notification user interface 690 and to display the user interface that was being displayed prior to notification user interface 690 being displayed.

At FIG. 6V, computer system 600 receives tap input 6500 on open user-interactive graphical user interface object 694b and, in response, displays mindfulness user interface 620a.

FIGS. 6W-6X illustrate exemplary user interfaces for configuring mindfulness notifications in accordance with some embodiments. The user interfaces in these figures are used to illustrate the processes described below, including the processes in FIG. 7.

FIGS. 6W and 6X illustrate computer system 695 (e.g., an electronic device) displaying, via display 696, notification configuration user interfaces 697a and 697b, respectively. In some embodiments, computer system 695 optionally includes one or more features of device 100, device 300, or device 500. In some embodiments, computer system 600 is a tablet, phone, laptop, desktop, camera, etc. In some embodiments, the settings for notifications related to the mindfulness application can be created, edited, and/or configured via computer system 600 or computer system 695. FIGS. 6W and 6X illustrate representative user interfaces for configuring settings for notifications related to the mindfulness application via computer system 695, which is in wireless communication with computer system 600. In some embodiments, the notification settings that are configured via computer system 695 are wirelessly transmitted to computer system 600. In some embodiments, computer system 600 and computer system 695 are paired. In some embodiments, computer system 600 and computer system 695 are logged into the same account. In some embodiments, information related to the mindfulness notification settings are wirelessly transmitted from computer system 695 to computer system 600 in accordance with a determination that computer system 600 and computer 695 are both logged into a same user account.

At FIG. 6W, computer system 695 displays notification configuration user interface 697a. Notification configuration user interface 697a includes options for configuring notifications to be displayed (e.g., via computer system 600 and/or computer system 695) based on certain conditions (e.g., at a particular time of day). Notification configuration user interface 697a includes settings for the frequency of mindfulness notifications, including allow setting 697a1, which allows notifications to be displayed, center setting 697a2, which sends notifications to a notification center instead of allowing mindfulness notifications to be displayed as full-screen notifications, and off setting 697a3, which turns off mindfulness notifications. Notification configuration user interface 697a includes selection indicator 693 (e.g., a checkmark), which is displayed on (e.g., next to) a currently selected setting for mindfulness notifications to indicate which setting is currently selected.

Notification configuration user interface 697a further includes mindfulness notification timer 698a1 and mindfulness notification timer 698a2, which correspond to settings for displaying mindfulness notifications at particular times of day. For example, mindfulness notification timer 698a1 corresponds to displaying a notification at 7:00 A.M. every day, whereas mindfulness notification timer 698a2 corresponds to displaying a notification at 10:00 P.M. every day. In some embodiments, mindfulness notifications timers 698a1 and 698a2 can be toggled on or off via a tap inputs.

Notification configuration user interface 697a further includes options for generating mindfulness notifications with certain qualities. For example, notification configuration user interface 697a includes haptics setting 698c which, when selected, displays options for generating (or not generating) haptics (e.g., vibrations) when a mindfulness notification is generated. For example, mindfulness notifications can be generated with various degrees of haptic strength (e.g., no haptics, prominent haptics, weak haptics).

Notification configuration user interface 697a further includes options for executing mindfulness functions (e.g., breathe, reflect) with certain settings. For example, notification configuration user interface 697a includes breath rate setting 698d which, when selected, displays options for starting (e.g., launching) a breathe function from a mindfulness notification with a particular (e.g., default) number of breaths. For example, at FIG. 6W, the currently selected breath rate setting 698d is 7 breaths. Further, notification configuration user interface 697a includes previous breathe toggle 698e and previous reflect duration toggle 698f In some embodiments, previous breathe toggle 698e and previous reflect duration toggle 698f can be selected to configure mindfulness notifications so that launching a particular mindfulness function from a mindfulness notification will cause the function (e.g., the breathe function or the reflect function) to be executed for the same duration that the function had executed for the previous time that the function executed.

Notification configuration user interface 697a further includes add user-interactive graphical user interface object 698b, which, when selected, causes computer system 695 to display notification configuration user interface 697b, which includes options for creating new mindfulness notification timers.

At FIG. 6W, computer system 695 detects tap input 650p on add user-interactive graphical user interface object 698b.

At FIG. 6X, in response to detecting tap input 650p, computer system 695 displays notification configuration user interface 697b. Notification configuration user interface 697b includes options for adding a new mindfulness notification tinier with particular settings. For example, notification configuration user interface 697b includes default time 699a, which indicates the currently selected time at which the mindfulness notification timer will be configured to generate mindfulness notifications. Notification configuration user interface 697b further includes day 699b, which indicates the current days that the mindfulness notification timer will generate mindfulness notifications on (e.g., weekdays, weekends, 7 days a week). Notification configuration user interface 697b further includes keypad 699, which can be used to edit default time 699a via tap inputs. Notification configuration user interface 697b further includes save user-interactive graphical user interface object 699d which, when selected, saves the configured mindfulness notification timer with the currently selected settings, and causes computer system 600 and/or computer system 695 to generate mindfulness notifications in accordance with the selected settings.

FIG. 7 is a flow diagram illustrating a method for recording the execution duration of functions using a computer system in accordance with some embodiments. Method 700 is performed at a computer system (e.g., 100, 300, 500, a wearable electronic device (e.g., a smartwatch), a smartphone, a desktop computer, a laptop, a tablet) that is in communication with a display generation component (e.g., a display controller, a touch-sensitive display system), one or more input devices (e.g., a touch-sensitive surface, a button, a mouse, a keyboard), and one or more sensors (e.g., an accelerometer, a heart rate monitor, a pressure sensor). Some operations in method 700 are, optionally, combined, the orders of some operations are, optionally, changed, and some operations are, optionally, omitted.

As described below, method 700 provides an intuitive way for recording the execution duration of functions. The method reduces the cognitive burden on a user for recording the execution duration of functions, thereby creating a more efficient human-machine interface. For battery-operated computing devices, enabling a user to record the execution duration of functions faster and more efficiently conserves power and increases the time between battery charges.

The computer system (e.g., 600) displays (702), via the display generation component, a first user interface (e.g., 620a) (e.g., a watch user interface) that concurrently includes a first user-interactive graphical user interface object (e.g., 608) (e.g., an affordance) and a second user-interactive graphical user interface object (e.g., 610). The first user-interactive graphical user interface object, when selected, initiates (e.g., launches, starts, causes to begin executing, displays a user interface that includes an option for launching the function with a selection (e.g., launching the function for a selected number of minutes, launching the function with a selected media item)) execution of a first function, where the first function includes (e.g., wherein executing the first function includes) measuring, via the one or more sensors, a first physiological parameter (e.g., heart rate, blood oxygen level, $VO_2$ max, ECG; measuring a physiological parameter of a user of the computer system). In some embodiments, the first function executes for a predetermined period of time after being initiated. The second user-interactive graphical user interface object, when selected, initiates execution of (e.g., launches, starts, causes to begin executing) a second function different from the first function, wherein the second function includes (e.g., wherein executing the second function includes) measuring, via the one or more sensors, a second physiological parameter. In some embodiments, the second function executes for a predetermined period of time after being initiated. In some embodiments, the first physiological parameter and the second physiological parameter are the same.

The computer system (e.g., 600) receives (704), via the one or more input devices, a first set of one or more inputs that includes a first input (e.g., 650a) (e.g., a tap input, a press input) corresponding to the first user-interactive graphical user interface object (e.g., 608). In response to receiving the first set of one or more inputs, the computer system executes (706) the first function.

After executing the first function (e.g., after the first function has completed execution, while the first function continues to execute, and/or in some embodiments, after the first and second functions have been initiated and/or executed during a predetermined period of time), the computer system (e.g., 600) displays (708) a second user interface (e.g., 640d) that includes a visual representation of a first duration of time (e.g., 662a) (e.g., text indicating a number of minutes, hours, and/or days), wherein the first duration of time includes a first amount of cumulative time (e.g., first amount of combined time) that the first function has been executed (e.g., the amount of time during which the function has been running) within a predetermined time period (e.g., the current day) and a second amount of cumulative time that the second function has been executed during the predetermined time period (e.g., the first duration of time is the cumulative amount of time that the first and the second functions have executed during the predetermined period of time). In some embodiments, in response to detecting the termination of execution of the first function, the computer system displays the second user interface. In some embodiments, the amount of time that a function has executed is determined independent of physiological measurements taken while the function is executing. In some embodiments, the amount of time that a function has executed is the same regardless of the activity level (e.g., exertion) of a user. In some embodiments, the amount of time that a function has executed is based on the amount of time that a user interface corresponding to the function being executed has been displayed via the display generation component. Concurrently displaying a first user-interactive graphical user interface object that, when selected, initiates execution of a first function and a second user-interactive graphical user interface object that, when selected, initiates execution of a second function, wherein the time that the first function and the second function are executed is aggregated into a first duration of time enables the user to quickly and efficiently initiate execution of the first function or the second function from the same user interface, and provides visual feedback about the relationship between the first function and the second function (e.g., that they share a timer). Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, the computer system (e.g., 600) receives, via the one or more input devices, a second set of one or more inputs that includes a second input (e.g., 650*h*) (e.g., a tap input, a press input) corresponding to the second user-interactive graphical user interface object (e.g., 610), In response to receiving the second set of one or more inputs, the computer system executes the second function. In some embodiments, after executing the second function, the computer system displays a third user interface (e.g., 678*d*) that includes a visual representation of a duration of time (e.g., 662*b*) (e.g., text indicating a number of minutes, hours, and/or days), wherein the duration of time includes a third amount of cumulative time (e.g., first amount of combined time) that the first function has been executed (e.g., the amount of time during which the function has been running) within the predetermined time period (e.g., the current day) and a fourth amount of cumulative time that the second function has been executed during the predetermined time period (e.g., the duration of time is the cumulative amount of time that the first and the second functions have executed during the predetermined period of time). In some embodiments, executing the second function includes displaying a visualization corresponding to the second function, Executing the second function in response to receiving a second set of one or more inputs received while the computer system is displaying the first user interface enables the user to quickly and easily cause the second function to begin executing from the first user interface, thereby reducing the number of inputs required to cause the second function to begin executing while the first user interface is displayed. Reducing the number of inputs needed to perform an operation enhances the operability of the system and makes the computer system more efficient (e.g., by helping the user to quickly and easily initiate execution of a second function after initiating execution of a first function) which, additionally, reduces power usage and improves battery life of the device by enabling the user to use the system more quickly and efficiently.

In some embodiments, executing the first function includes displaying a first measurement of the first physiological parameter (e.g., 636) (e.g., text representing the current value of the physiological measurement). In some embodiments, executing the second function includes foregoing displaying (e.g., does not include displaying) a measurement of the second physiological parameter. In some embodiments, executing the second function does not include a measurement of any physiological parameter. Displaying a measurement of the first physiological parameter while the first function is executing but foregoing displaying a measurement of the second physiological parameter while the second function is executing provides visual feedback about the relevant details of the function being executed (e.g., by displaying the physiological parameter during a function wherein displaying the measurement of the physiological parameter is relevant to the function as it is executing without displaying the physiological parameter during a function wherein displaying the measurement of the physiological parameter would not be relevant to the function as it is executing). Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, displaying the first user interface (620*a*) includes displaying a current time (e.g., 606) (e.g., a current time of day; the current time in the current time zone). In some embodiments, executing the first function includes displaying a first function user interface (e.g., 640*a*) that includes an indication of the current time (e.g., 634). In some embodiments, executing the second function includes displaying a second function user interface (e.g., 680*a*) that does not include the indication of the current time (e.g., any indication of the current time). In some embodiments, the time indicator is continuously or periodically updated with the passage of time to reflect the current time of day. In some embodiments, the time indicator is coordinated with and/or intended to reflect the coordinated universal time with an offset based on a currently selected time zone. In some embodiments, executing the second function includes foregoing display of the current time (e.g., displaying a user interface that does not include the current time). In some embodiments, the computer system resumes displaying the current time after the second function has executed. In some embodiments, in accordance with a determination that the first function is executing, the computer system enters a lower-power mode predetermined amount of time (e.g., by lowering the brightness of the display). In some embodiments, in accordance with a determination that the second function is executing, the computer system forgoes entering the lower-power mode after the predetermined amount of time while the second function is executing. Displaying a user interface that includes an indication of the current time as part of executing the first function but displaying a user interface that does not include the indication of the current time as part of executing the second function provides visual feedback about the relevant details of the function being executed (e.g., by displaying the physiological parameter during a function wherein the current time is relevant/helpful to the function as it is executing without displaying the current time during a function wherein displaying the measurement of the physiological parameter would not be relevant/helpful to the function as it is executing). Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently. Moreover, automatically displaying a user interface that does or does not include an indication of the current time depending on which function is executing enables the appropriate information to be displayed based on which function is executing, without requiring the user to provide multiple inputs to function accordingly (e.g., to turn off display of the current time while a particular function is executing). Performing an operation when a set of conditions has been met without requiring further user input enhances the operability of the device and makes the user-device interface more efficient (e.g., by helping the user interface to be displayed based on which function is currently executing) which, additionally, reduces power usage and improves battery life of the device by enabling the user to use the device more quickly and efficiently.

In some embodiments, executing the first function includes causing audio playback (e.g. of a media item (e.g., an audio track, a music track, a narrative voice track)) (e.g., playback of a track in playlist 626), In some embodiments, executing the second function does not include causing audio playback. In some embodiments, executing the first function includes causing the audio playback via an audio output device that is in communication with the computer system. Executing a first function and/or a second function, wherein executing the first function includes causing audio playback and wherein executing the second function does not include causing audio playback enables the appropriate media elements (e.g., an audio component) to be played during a function without requiring the user to manually begin playback of the function and an audio component associated with the function if the function is associated with an audio component. Performing an operation when a set of conditions has been met without requiring further user input enhances the operability of the device and makes the user-device interface more efficient (e.g., by playing an audio component when executing a function if there is an audio component associated with the function being executed) which, additionally, reduces power usage and improves battery life of the device by enabling the user to use the device more quickly and efficiently.

In some embodiments, after receiving the first input (e.g., 650*a*) of the first set of one or more inputs and prior to executing the first function, the computer system (e.g., 600) displays a third user interface (e.g., 630*a*) (e.g., a configuration interface for configuring one or more audio aspects of the first function) that includes a third user-interactive graphical user interface object (e.g., 614*c*) that, when selected, initiates a process for selecting a first audio media item (e.g., an audio track, a music track, a narrative voice track) to be played as part of executing the first function. In some embodiments, the third user interface includes a plurality of affordances that correspond to respective audio media items for selection. After receiving the second input (e.g., 650*h*) of the second set of one or more inputs and prior to executing the second function, the computer system displays a fourth user interface (e.g., 670*b*) (e.g., a configuration interface for configuring one or more audio aspects of the first function) that includes a fourth user-interactive graphical user interface object (e.g., 676*a*) that, when selected, initiates a process for selecting a duration for execution of the second function. Displaying a third user interface that includes a user-interactive graphical user interface object that, when selected initiates a process for selecting a first audio media item to be played as part of the first function and, after receiving the second input of the second set of one or more inputs and prior to executing the second function, displaying a fourth user interface that includes a fourth user-interactive graphical user interface object that, when selected, initiates a process for selecting a duration for execution of the second function provides visual feedback about the relevant details required to finish initiating the execution of each respective function (e.g., selecting a media item or selecting a time duration). Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, while displaying the fourth user interface (e.g., 670*b*), the computer system (e.g., 600) displays a second visual representation (e.g., 674) of a currently selected duration with a first duration value. While displaying the fourth user interface, the computer system receives, via the one or more input devices, a third set of one or more inputs that includes a third input (e.g., 650*k*1, 650*k*2) (e.g., a tap input, a press input, a rotation of a rotatable input mechanism) corresponding to a request to change the currently selected duration. While displaying the fourth user interface and in response to receiving the third input corresponding to a request to change the currently selected duration, the computer system updates the second visual representation of the currently selected duration to be displayed with a second duration value different from the first duration value, Displaying a user interface that includes a visual representation of the currently selected duration with a first duration value and, in response to receiving an input, updating the second visual representation of the currently selected duration to be displayed with a second duration value provides visual feedback about the currently selected duration for which the second function will be executed, including an updated duration after the currently selected duration value after the request to change the currently selected duration is received. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently. Further, displaying selection options (e.g., for selecting a media track or a duration) in response to selecting a user-interactive graphical user interface object that, when selected, initiates execution of a function enables a user to quickly and easily make selections about function-specific criteria before the respective function begins executing, thereby reducing the number of inputs required to execute the respective function with the given selections. Reducing the number of inputs needed to perform an operation enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, after displaying the first user interface (e.g. 620*a*), the computer system (e.g., 600) receives a swipe input (e.g., 650*d*1, 650*d*2). In accordance with a determination that the swipe input was received while the first function is executing (and, in some embodiments, in accordance with a determination that a playback progress indicator is displayed while the swipe input is received), the computer system displays, via the display generation component, a set of playback controls (e.g., 642, 644*a*, 644*b*)

(e.g., one or more selectable user interface objects) for modifying media playback (e.g., audio playback) of media associated with the second function. In accordance with a determination that the swipe input was received while the second function is executing (and, in some embodiments, in accordance with a determination that a visualization corresponding to the second function is displayed while the swipe input is received), the computer system foregoes displaying the set of playback controls. In some embodiments, in accordance with a determination that the swipe input was received while the second function is executing, the computer system foregoes displaying any playback controls. Displaying a set of playback controls in response to receiving a swipe input while a first function is executing, but foregoing displaying playback controls in response to receiving a swipe input while a second function is executing provides visual feedback about whether the function currently being executed is associated with playback controls (e.g., one function may allow the user to select play/pause, while another function might not include play/pause functionality). Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, executing the first function includes concurrently displaying a representation of time that corresponds to execution of the first function (e.g., 632) (e.g., an amount of elapsed time since the start of the first function, a remaining time until completion of the first function) and a second measurement of the first physiological parameter (e.g., 636) (e.g., a heart rate value). Executing the first function, wherein executing the first function includes concurrently displaying a representation of time that corresponds to execution of the first function and a second measurement of a physiological parameter provides visual feedback about the relevant details of a function by concurrently displaying information about the playback progress of a media item (e.g., a playback position within the media item) and a physiological measurement. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, displaying the second user interface (e.g., 640a1) includes displaying, via the display generation component, a third measurement of the first physiological parameter (e.g., 636) taken (e.g., recorded, measured) during the first amount of cumulative time. In some embodiments, displaying the second user interface includes displaying the third measurement of the first physiological parameter taken during the first amount of cumulative time without including measurements of the first physiological parameter taken during additional time included in the first duration of time (e.g., the second amount of cumulative time). Displaying a second user interface including a measurement of the first physiological parameter taken during the first amount of cumulative time (e.g., without including measurements of the physiological parameter taken during time outside of the first amount of cumulative time) provides visual feedback about the physiological parameter during while the function was executing (e.g., at a time when the measurement might be relevant) as opposed to measurements taken at another time. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, the computer system (e.g., 600) executes the first function for a second duration of time. After executing the first function for the second duration of time, the computer system displays a first iteration of the second user interface (e.g., 640d), where the first iteration of the second user interface includes a visual representation of the second duration of time (e.g., 662a). In some embodiments, the visual representation of the second duration of time includes the number of minutes during which the first function has executed without providing an indication of the number of seconds during which the first function has executed. After executing a duration of time, displaying a first iteration of the second user interface, wherein the first iteration of the second user interface includes a visual representation of the second duration of time provides visual feedback about the amount of time that the function was executing for. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, the first iteration of the second user interface (e.g., 640d) includes a fifth user-interactive graphical user interface object (e.g., 666) for ceasing to display the second user interface. In some embodiments, the computer system (e.g., 600) receives a fourth input (e.g., 650g) that corresponds to selection (e.g., a user input that corresponds to a selection) (e.g., a tap gesture, a swipe, a press input, and/or a mouse click) of the fifth user-interactive graphical user interface object for ceasing to display the second user interface. In response to receiving the fourth input that corresponds to selection of the fifth user-interactive graphical user interface object for ceasing to display the second user interface, the computer system returns to the first user interface (e.g., 620a). In some embodiments, returning to the first user interface includes displaying, via the display generation component, the first user interface that concurrently includes the first user-interactive graphical user interface object that, when selected, initiates execution of the first function, where the first function includes measuring, via the one or more sensors, the first physiological parameter, and the second user-interactive graphical user interface object that, when selected, initiates execution of the second function different from the first function, where the second function includes measuring, via the one or more sensors, the second physiological parameter. Displaying a user-interactive graphical user interface object for ceasing to display the second user interface in the second user interface and, in response to selecting the user-interactive graphical user interface object for ceasing to display the second user interface, returning to the first user interface enables the user to quickly and easily transition directly from the second user interface to the first user interface (e.g., to initiate execution of another function), thereby reducing the number of inputs required to display the first user interface after displaying the second user interface. Reducing the number of inputs needed to perform an operation enhances the operability of the system and makes the computer system more efficient (e.g., by helping the user to quickly and easily initiate execution of a second function after initiating execution of a first function) which, additionally, reduces power usage and improves battery life of the device by enabling the user to use the system more quickly and efficiently.

In some embodiments, after returning to the first user interface (e.g., 620*b*), while displaying the first user interface, the computer system (e.g., 600) receives, via the one or more input devices, a fourth set of one or more inputs that includes an fifth input (e.g., 650*h*) (e.g., a tap input, a press input) corresponding to the second user-interactive graphical user interface object (e.g., 610), In response to receiving the fourth set of one or more inputs, the computer system executes the second function. Receiving an input corresponding to the second user-interactive graphical user interface object after returning to the first user interface and while displaying the first user interface and, in response to receiving the input, initiating execution of the second function, enables the user to quickly and easily transition directly from the second user interface directly back to the first user interface (e.g., to initiate execution of another function), thereby reducing the number of inputs required to initiate execution of a second function after initiating execution of a first function. Reducing the number of inputs needed to perform an operation enhances the operability of the system and makes the computer system more efficient (e.g., by helping the user to quickly and easily initiate execution of a second function after initiating execution of a first function) which, additionally, reduces power usage and improves battery life of the device by enabling the user to use the system more quickly and efficiently.

In some embodiments, after executing the second function (e.g., after the second function has completed execution, while the second function continues to execute), the computer system (e.g., 600) displays a second iteration of the second user interface (e.g., 678*d*) (e.g., in response to detecting the termination of execution of the second function) that includes a third visual representation of a third duration of time (e.g., 662*b*) (e.g., text indicating a number of minutes, hours, and/or days). In some embodiments, the third duration of time includes the first amount of cumulative time (e.g., first amount of combined time) that the first function has been executed (e.g., the amount of time during which the function has been running) within the predetermined time period (e.g., the current day), and an updated second amount of cumulative time that the second function has been executed during the predetermined time period. In some embodiments, the updated second amount of cumulative time that the second function has been executed during the predetermined time period includes additional time that the second function has executed for. In some embodiments, the second duration of time has increased relative to the first duration of time by the same amount as the updated second amount of cumulative time relative to the second amount of cumulative time. After executing the second function, displaying the second user interface that includes a third visual representation of a second duration of time, wherein the second duration of time includes the first amount of cumulative time that the first function has been executed within a predetermined time period and an updated second amount of cumulative time that the second function has been executed during the predetermined time period provides visual feedback about the fact that the second function has been executed for additional time since the second user interface was previously displayed (e.g., prior to returning to the first user interface), and provides improved visual feedback about the cumulative time as indicated by the updated second amount of cumulative time included in the second duration of time. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, while executing the first function, the computer system (e.g., 600) displays a sixth user-interactive graphical user interface object (e.g., 648*c*) for displaying (e.g., launching, executing) a workout application (e.g., a fitness application different from the application that corresponds to the first function and/or the first user interface). While executing the first function, the computer system receives a sixth input (e.g., 650*e*) that corresponds to selection (e.g., a user input that corresponds to a selection) (e.g., a tap gesture, a swipe, a press input, and/or a mouse click) of the sixth user-interactive graphical user interface object for displaying the workout application. While executing the first function and in response to receiving the sixth input that corresponds to selection of the sixth user-interactive graphical user interface object for displaying the workout application, the computer system displays, via the display generation component, a workout application user interface (e.g., 660*a*). Displaying a user-interactive graphical user interface object for displaying a workout application while executing the first function enables the user to quickly and easily launch the workout application while executing the first function, thereby reducing the number of inputs required to initiate execution of the workout application while the first function is being executed. Reducing the number of inputs needed to perform an operation enhances the operability of the system and makes the computer system more efficient (e.g., by helping the user to quickly and easily launch the workout application while the first function is executing) which, additionally, reduces power usage and improves battery life of the device by enabling the user to use the system more quickly and efficiently.

In some embodiments, while executing the first function and after displaying the workout application user interface (e.g., 660*a*), the computer system (e.g., 600) receives, via the one or more input devices, a fifth set of one or more inputs that includes a seventh input (e.g., 650*l*) corresponding to a request to initiate execution of a workout tracking function different from the first function (e.g., a tap input, a press input) (e.g., an input corresponding to a request to initiate execution of a third function of the workout application different from the first function, and, in some embodiments, the third function is different from the second function). While executing the first function and in response to receiving the fifth set of one or more inputs, the computer system executes the workout tracking function while continuing execution of the first function. While executing the first function, receiving an input corresponding to a request to initiate execution of a workout tracking function different from the first function, in response to receiving the request to initiate execution of the workout tracking function, concurrently executing the third function enables the user to quickly and easily initiate execution of a workout tracking function while executing the first function. Reducing the number of inputs needed to perform an operation enhances the operability of the system and makes the computer system more efficient (e.g., by helping the user to quickly and easily initiate execution of a workout tracking function while the first function is executing) which, additionally, reduces power usage and improves battery life of the device by enabling the user to use the system more quickly and efficiently.

In some embodiments, after concurrently executing the first function and the workout tracking function for a third duration of time, the computer system (e.g., 600) determines that the first function has stopped executing (e.g., concluded). After determining that the first function has stopped executing, the computer system continues executing the workout tracking function for a fourth duration of time. After continuing execution of the workout tracking function for the fourth duration of tune, the computer system displays, via the display generation component, a third iteration of the second user interface (e.g., 640*d*) that includes a fourth visual representation of a fifth duration of time (e.g., 662*a*) (e.g., text indicating a number of minutes, hours, and/or days), where the fifth duration of time includes the third duration of time that the first function has been executed (e.g., the amount of time during which the function has been running) within a predetermined time period without including the fourth duration of time (e.g., time when the third function was being executed without the first function executing). After concurrently executing a first function and a second function for a third duration of time, determining that the first function has stopped executing and, after determining that the first function has stopped executing, continuing execution of the third function for a fourth duration of time and displaying a user interface including a fourth visual representation of a fifth duration of time, wherein the fifth duration of time includes the third duration of time that the first function has been executed within a predetermined time period without including the fourth duration of time provides visual feedback that the time during which the third function was being executed without the first function executing is not tracked in the shared duration displayed on the user interface. Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently. Automatically including time that the first function is executing in the fifth duration of time without including the fourth duration of time that the third function was being executed without the first function executing enables the user to track the time during which certain functions are executing without tracking the time that other functions are executing. Performing an operation when a set of conditions has been met without requiring further user input enhances the operability of the device and makes the user-device interface more efficient (e.g., by helping the user interface to automatically track the time spent executing certain functions) which, additionally, reduces power usage and improves battery life of the device by enabling the user to use the device more quickly and efficiently.

In some embodiments, the first user interface (e.g., 620*b*) includes a seventh user-interactive graphical user interface object (e.g., 612*b*) that, when selected, initiates execution of (e.g., launches, starts, causes to begin executing, displays a user interface that includes an option for launching the function with a selection (e.g., launching the function for a selected number of minutes, launching the function with a selected media item)) a third function different from the first function and the second function, where the third function includes (e.g., wherein executing the third function includes) measuring, via the one or more sensors, a third physiological parameter. In some embodiments, the third physiological parameter is the same as the first physiological parameter and/or the second physiological parameter. While displaying the first user interface, the computer system (e.g., 600) receives, via the one or more input devices, a sixth set of one or more inputs that includes an eighth input (e.g., 650*i*) (e.g., a tap input, a press input) corresponding to the seventh user-interactive graphical user interface object. In response to receiving the sixth set of one or more inputs, the computer system executes the third function. Concurrently displaying a first user-interactive graphical user interface object that, when selected, initiates execution of a first function and a second user-interactive graphical user interface object that, when selected, initiates execution of a second function, and a seventh user-interactive graphical user interface object that, when selected, initiates execution of a third function different from the first function and the second function, enables the user to quickly and efficiently initiate execution of the first function, the second function from the same user interface, or the third function from the same user interface, thereby reducing the number of inputs required to initiate the first function, the second function, or the third function (e.g., by requiring the user to navigate to various user interfaces to initiate execution of the functions). Reducing the number of inputs needed to perform an operation enhances the operability of the system and makes the computer system more efficient (e.g., by helping the user to quickly and easily initiate execution of the first function, the second function, and the third function) which, additionally, reduces power usage and improves battery life of the device by enabling the user to use the system more quickly and efficiently.

In some embodiments, after executing the third function, the computer system 600) displays a fifth user interface (e.g., 682*d*) (and, in some embodiments, in response to detecting the termination of execution of the third function, the computer system displays the fifth user interface) that includes a fifth visual representation of a sixth duration of time (e.g., 662*c*) (e.g., text indicating a number of minutes, hours, and/or days), where the sixth duration of time includes the first amount of cumulative time (e.g., first amount of combined time) that the first function has been executed (e.g., the amount of time during which the function has been running) within the predetermined time period (e.g., the current day), the second amount of cumulative time that the second function has been executed during the predetermined time period, and a third amount of cumulative time that the third function has been executed during the predetermined time period. Displaying a user interface that includes a visual representation of a duration of time, wherein the duration of time includes the first amount of cumulative time that the first function has been executed within the predetermined time period, the second amount of cumulative time that the second function has been executed during the predetermined time period, and a third amount of cumulative time that the third function has been executed during the predetermined time period provides visual feedback about the relationship between the first function. the second function, and the third function (e.g., that they share a tinier). Providing improved visual feedback to the user enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently.

In some embodiments, the computer system (e.g., 600) displays a notification (e.g., 692) corresponding to the second function based on a determination about a current time (e.g., a current time of day; the time in the current time zone). In some embodiments, the time indicator is continuously or periodically updated with the passage of time to reflect the current time of day. In some embodiments, the time indicator is coordinated with and/or intended to reflect the coordinated universal time with an offset based on a currently selected time zone. While displaying the notification, the computer system receives, via the one or more input devices, a ninth input (e.g., 650o) (e.g., a tap input, a press input, a mouse click) corresponding to the notification corresponding to the second function. In response to receiving the ninth input, the computer system displays a sixth user interface (e.g., 620a) that includes an eighth user-interactive graphical user interface object that, when selected, initiates execution of the second function. In some embodiments, the second function begins executing in response to the eighth user input. Displaying a user interface that includes an eighth user-interactive graphical user interface object that, when selected, initiates execution of the second function in response to an input on the notification corresponding to the second function enables a user to quickly and easily initiate execution of the second function after receiving a notification corresponding to the second function, thereby reducing the number of inputs required to transition from displaying the notification to viewing information about the watch face and/or downloading the watch face. Reducing the number of inputs needed to perform an operation enhances the operability of the system and makes the computer system more efficient (e.g., by helping the user to provide proper inputs and reducing user mistakes when operating/interacting with the system) which, additionally, reduces power usage and improves battery life of the device by enabling the user to use the system more quickly and efficiently. Further, displaying the notification corresponding to the second function that, when selected, initiates execution of the second function enables the user to quickly and easily initiate execution of the second function via the notification, thereby reducing the number of inputs required to initiate execution of the second function. Reducing the number of inputs needed to perform an operation enhances the operability of the system and makes the computer system more efficient (e.g., by helping the user to quickly and easily initiate execution of the second function via the notification) which, additionally, reduces power usage and improves battery life of the device by enabling the user to use the system more quickly and efficiently.

In some embodiments, the determination about the current time is at least partially based on a determination that the current time is a first offset amount of time away (e.g., by a number of minutes) from an alarm time (e.g., a time at which an alarm is scheduled to go off). Automatically determining whether the current time is an offset amount of time away from an alarm time enables the notifications related to a function to be automatically generated based on the current time, which can then prompt a user of the computer system to execute the function based on a current time. Performing an operation when a set of conditions has been met without requiring further user input enhances the operability of the device and makes the user-device interface more efficient (e.g., by automatically determining whether the current time is an offset amount of time away from an alarm time without requiring the user to determine whether the current time is the offset amount of time away from the alarm time manually) which, additionally, reduces power usage and improves battery life of the device by enabling the user to use the device more quickly and efficiently.

In some embodiments, the determination about the current time is at least partially based on a determination that the current time is a second offset amount of time away (e.g., by a number of minutes) from a predetermined bedtime and/or a predetermined wake up time. In some embodiments, the predetermined bedtime and/or wakeup time can be set by a user of the computer system. Automatically determining whether the current time is an offset amount of time away from a predetermined bedtime and/or a predetermined wake up time enables the notifications related to a function to be automatically generated based on the current time, which can then prompt a user of the computer system to execute the function based on a current time. Performing an operation when a set of conditions has been met without requiring further user input enhances the operability of the device and makes the user-device interface more efficient (e.g., by automatically determining whether the current time is an offset amount of time away from a predetermined bedtime and/or a predetermined wake up time without requiring the user to determine whether the current time is the offset amount of time away from the predetermined bedtime and/or a predetermined wake up time manually) which, additionally, reduces power usage and improves battery life of the device by enabling the user to use the device more quickly and efficiently.

In some embodiments, the determination about the current time is at least partially based on a determination that the current time is a third offset amount of time away (e.g., by a number of minutes) from a predetermined (e.g., automatically predetermined) expected bedtime and/or predetermined (e.g., automatically predetermined) expected wake up time. In some embodiments, the predetermined expected bedtime and/or the predetermined expected wake up time are determined by the computer system based at least partially on the times at which a user uses the computer system. Automatically detecting an expected bedtime and/or an expected wake up time and determining whether the current time is an offset amount of time away from the automatically detected expected bedtime and/or the automatically detected expected wake up time enables the notifications related to a function to be automatically generated based on the current time, which can then prompt a user of the computer system to execute the function based on a current time. Performing an operation when a set of conditions has been met without requiring further user input enhances the operability of the device and makes the user-device interface more efficient (e.g., by automatically determining whether the current time is an offset amount of time away from the automatically detected expected bedtime and/or the automatically detected expected wake up time without requiring the user to determine whether the current time is the offset amount of time away from the automatically detected expected bedtime and/or the automatically detected expected wake up time manually) which, additionally, reduces power usage and improves battery life of the device by enabling the user to use the device more quickly and efficiently.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the tracking of duration execution of related functions. The present disclosure contemplates that in some instances, this gathered data may include personal information data that uniquely identifies or can be used to contact or locate a specific person. Such personal information data can include demographic data, location-based data, telephone numbers, email addresses, twitter Ds, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to display function-related notifications at times based on user activity. Accordingly, use of such personal information data enables users to have calculated control of the displayed notifications. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health. Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of or access to, personal information data. That is, the present disclosure contemplates that hardware and/or software elements can be provided to prevent or block access to such personal information data. For example, in the case of function-related notifications, the present technology can be configured to allow users to select to "opt in" or "opt out" of participation in the collection of personal information data during registration for services or anytime thereafter. In another example, users can select not to provide bedtime and wake time data for tailored function-related notifications. In yet another example, users can select to limit the length of time for which bedtime and wake time data is maintained or entirely prohibit sharing of bedtime or wake time data. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, function-related notifications can be selected and delivered to users by inferring preferences based on non-personal information data or a bare minimum amount of personal information, such as the content being requested by the device associated with a user, other non-personal information available to the notification-generation setting and/or modules, or publicly available information.

What is claimed is:

1. A computer system that is configured to communicate with a display generation component, one or more input devices, and one or more sensors, the computer system comprising:
   one or more processors; and
   memory storing one or more programs configured to be executed by the one or more processors, the one or more programs including instructions for:

displaying, via the display generation component, a first user interface that concurrently includes:
- a first user-interactive graphical user interface object that, when selected, initiates execution of an audio meditation function; and
- a second user-interactive graphical user interface object that, when selected, initiates execution of a second function different from the audio meditation function;

receiving, via the one or more input devices, a first set of one or more inputs that includes a first input corresponding to the first user-interactive graphical user interface object;

in response to receiving the first set of one or more inputs:
- executing, for a first period of time, the audio meditation function, wherein executing the audio meditation function includes measuring, for the first period of time, via the one or more sensors, a first physiological parameter; and
- displaying a first measurement of the first physiological parameter during the first period of time;

while executing the audio meditation function, displaying, in an audio meditation user interface, a third user-interactive graphical user interface object for displaying a workout application during the first period of time;

receiving, via the one or more input devices, a second set of one or more inputs that includes selection of the third user-interactive graphical user interface object;

in response to receiving the second set of one or more inputs, executing a workout tracking function while continuing execution of the audio meditation function;

receiving, via the one or more input devices, a third set of one or more inputs that includes a second input corresponding to the second user-interactive graphical user interface object;

in response to receiving the third set of one or more inputs:
- executing, for a second period of time, the second function, wherein executing the second function includes measuring, for the second period of time, via the one or more sensors, a second physiological parameter; and
- foregoing displaying, for the entire duration of the second period of time in which the second physiological parameter is measured, a measurement of the second physiological parameter;

after executing the audio meditation function, displaying a second user interface that includes:
- an average measurement of the first physiological parameter measured while executing the audio meditation function for the first period of time; and
- a visual representation of a first duration of time, wherein the first duration of time includes a first amount of cumulative time that the audio meditation function has been executed within a predetermined time period and a second amount of cumulative time that the second function has been executed during the predetermined time period; and after executing the second function, displaying a third user interface that includes:
- an average measurement of the second physiological parameter measured while executing the second function for the second period of time; and
- a visual representation of a second duration of time, wherein the second duration of time includes an updated first amount of cumulative time that the audio meditation function has been executed within the predetermined time period and an updated second amount of cumulative time that the second function has been executed during the predetermined time period.

2. The computer system of claim 1, wherein:
displaying the first user interface includes displaying a current time,
executing the audio meditation function includes displaying an audio meditation function user interface that includes an indication of the current time, and
executing the second function includes displaying a second function user interface that does not include the indication of the current time.

3. The computer system of claim 1, wherein executing the audio meditation function includes causing audio playback, and wherein executing the second function does not include causing audio playback.

4. The computer system of claim 1, the one or more programs further including instructions for:
after receiving the first input of the first set of one or more inputs and prior to executing the audio meditation function, displaying a fourth user interface that includes a fourth user-interactive graphical user interface object that, when selected, initiates a process for selecting a first audio media item to be played as part of executing the audio meditation function, and
after receiving the second input of the third set of one or more inputs and prior to executing the second function, displaying a fifth user interface that includes a fifth user-interactive graphical user interface object that, when selected, initiates a process for selecting a duration for execution of the second function.

5. The computer system of claim 4, the one or more programs further including instructions for:
while displaying the fifth user interface:
displaying a second visual representation of a currently selected duration with a first duration value;
receiving, via the one or more input devices, a fourth set of one or more inputs that includes a third input corresponding to a request to change the currently selected duration; and
in response to receiving the third input corresponding to a request to change the currently selected duration, updating the second visual representation of the currently selected duration to be displayed with a second duration value different from the first duration value.

6. The computer system of claim 1, the one or more programs further including instructions for:
after displaying the first user interface, receiving a swipe input;
in accordance with a determination that the swipe input was received while the audio meditation function is executing, displaying, via the display generation component, a set of playback controls for modifying media playback of media associated with the second function; and
in accordance with a determination that the swipe input was received while the second function is executing, foregoing displaying the set of playback controls.

7. The computer system of claim 1, wherein executing the audio meditation function includes concurrently displaying a representation of time that corresponds to execution of the audio meditation function and a second measurement of the first physiological parameter.

8. The computer system of claim 1, wherein displaying the second user interface includes displaying, via the display generation component, a third measurement of the first physiological parameter taken during the first amount of cumulative time.

9. The computer system of claim 1, the one or more programs further including instructions for:
executing the audio meditation function for a third duration of time; and
after executing the audio meditation function for the third duration of time, displaying a first iteration of the second user interface, wherein the first iteration of the second user interface includes a visual representation of the third duration of time.

10. The computer system of claim 9, wherein the first iteration of the second user interface includes a sixth user-interactive graphical user interface object for ceasing to display the second user interface, the one or more programs further including instructions for:
receiving a fourth input that corresponds to selection of the sixth user-interactive graphical user interface object for ceasing to display the second user interface; and
in response to receiving the fourth input that corresponds to selection of the sixth user-interactive graphical user interface object for ceasing to display the second user interface, returning to the first user interface, wherein returning to the first user interface includes displaying, via the display generation component, the first user interface that concurrently includes:
the first user-interactive graphical user interface object that, when selected, initiates execution of the audio meditation function, wherein the audio meditation function includes measuring, via the one or more sensors, the first physiological parameter; and
the second user-interactive graphical user interface object that, when selected, initiates execution of the second function different from the audio meditation function, wherein the second function includes measuring, via the one or more sensors, the second physiological parameter.

11. The computer system of claim 10, the one or more programs further including instructions for:
after returning to the first user interface, while displaying the first user interface:
receiving, via the one or more input devices, a fifth set of one or more inputs that includes a fifth input corresponding to the second user-interactive graphical user interface object; and
in response to receiving the fifth set of one or more inputs, executing the second function.

12. The computer system of claim 11, the one or more programs further including instructions for:
after executing the second function, displaying a second iteration of the second user interface that includes a third visual representation of a third duration of time, wherein the third duration of time includes the first amount of cumulative time that the audio meditation function has been executed within the predetermined time period, and an updated second amount of cumulative time that the second function has been executed during the predetermined time period.

13. The computer system of claim 1, the one or more programs further including instructions for:
while executing the audio meditation function:
displaying the third user-interactive graphical user interface object for displaying a workout application; and
receiving a sixth input that corresponds to selection of the third user-interactive graphical user interface object for displaying the workout application; and
in response to receiving the sixth input that corresponds to selection of the third user-interactive graphical user interface object for displaying the workout application, displaying, via the display generation component, a workout application user interface.

14. The computer system of claim 13, the one or more programs further including instructions for:
while executing the audio meditation function:
after displaying the workout application user interface, receiving, via the one or more input devices, a sixth set of one or more inputs that includes a seventh input corresponding to a request to initiate execution of a workout tracking function different from the audio meditation function; and
in response to receiving the sixth set of one or more inputs, executing the workout tracking function while continuing execution of the audio meditation function.

15. The computer system of claim 14, the one or more programs further including instructions for:
after concurrently executing the audio meditation function and the workout tracking function for a third duration of time:
determining that the audio meditation function has stopped executing;
after determining that the audio meditation function has stopped executing, continuing execution of the workout tracking function for a fourth duration of time; and
after continuing execution of the workout tracking function for the fourth duration of time, displaying, via the display generation component, a third iteration of the second user interface that includes a fourth visual representation of a fifth duration of time, wherein the fifth duration of time includes the third duration of time that the audio meditation function has been executed within the predetermined time period without including the fourth duration of time.

16. The computer system of claim 1, wherein the first user interface includes a seventh user-interactive graphical user interface object that, when selected, initiates execution of a third function different from the audio meditation function and the second function, wherein the third function includes measuring, via the one or more sensors, a third physiological parameter, the one or more programs further including instructions for:
while displaying the first user interface, receiving, via the one or more input devices, a seventh set of one or more inputs that includes an eighth input corresponding to the seventh user-interactive graphical user interface object; and
in response to receiving the seventh set of one or more inputs, executing the third function.

17. The computer system of claim 16, the one or more programs further including instructions for:
after executing the third function, displaying a sixth user interface that includes a fifth visual representation of a sixth duration of time, wherein the sixth duration of time includes the first amount of cumulative time that the audio meditation function has been executed within the predetermined time period, the second amount of cumulative time that the second function has been executed during the predetermined time period, and a third amount of cumulative time that the third function has been executed during the predetermined time period.

18. The computer system of claim 1, the one or more programs further including instructions for:
displaying a notification corresponding to the second function based on a determination about a current time;
while displaying the notification, receiving, via the one or more input devices, a ninth input corresponding to the notification corresponding to the second function; and
in response to receiving the ninth input, displaying a seventh user interface that includes an eighth user-interactive graphical user interface object that, when selected, initiates execution of the second function.

19. A non-transitory computer-readable storage medium storing one or more programs configured to be executed by one or more processors of a computer system that is in communication with a display generation component, one or more input devices, and one or more sensors, the one or more programs including instructions for:
displaying, via the display generation component, a first user interface that concurrently includes:
a first user-interactive graphical user interface object that, when selected, initiates execution of an audio meditation function; and
a second user-interactive graphical user interface object that, when selected, initiates execution of a second function different from the audio meditation function;
receiving, via the one or more input devices, a first set of one or more inputs that includes a first input corresponding to the first user-interactive graphical user interface object;
in response to receiving the first set of one or more inputs:
executing, for a first period of time, the audio meditation function, wherein executing the audio meditation function includes measuring, for the first period of time, via the one or more sensors, a first physiological parameter; and
displaying a first measurement of the first physiological parameter during the first period of time;
while executing the audio meditation function, displaying, in an audio meditation user interface, a third user-interactive graphical user interface object for displaying a workout application during the first period of time;
receiving, via the one or more input devices, a second set of one or more inputs that includes selection of the third user-interactive graphical user interface object;
in response to receiving the second set of one or more inputs, executing a workout tracking function while continuing execution of the audio meditation function;
receiving, via the one or more input devices, a third set of one or more inputs that includes a second input corresponding to the second user-interactive graphical user interface object;
in response to receiving the third set of one or more inputs:
executing, for a second period of time, the second function, wherein executing the second function includes measuring, for the second period of time, via the one or more sensors, a second physiological parameter; and
foregoing displaying, for the entire duration of the second period of time in which the second physiological parameter is measured, a measurement of the second physiological parameter;
after executing the audio meditation function, displaying a second user interface that includes:
an average measurement of the first physiological parameter measured while executing the audio meditation function for the first period of time; and
a visual representation of a first duration of time, wherein the first duration of time includes a first amount of cumulative time that the audio meditation function has been executed within a predetermined time period and a second amount of cumulative time that the second function has been executed during the predetermined time period; and
after executing the second function, displaying a third user interface that includes:
an average measurement of the second physiological parameter measured while executing the second function for the second period of time; and
a visual representation of a second duration of time, wherein the second duration of time includes an updated first amount of cumulative time that the audio meditation function has been executed within the predetermined time period and an updated second amount of cumulative time that the second function has been executed during the predetermined time period.

20. The non-transitory computer-readable storage medium of claim 19, wherein:
displaying the first user interface includes displaying a current time,
executing the audio meditation function includes displaying an audio meditation function user interface that includes an indication of the current time, and
executing the second function includes displaying a second function user interface that does not include the indication of the current time.

21. The non-transitory computer-readable storage medium of claim 19, wherein executing the audio meditation function includes causing audio playback, and wherein executing the second function does not include causing audio playback.

22. The non-transitory computer-readable storage medium of claim 19, the one or more programs further including instructions for:
after receiving the first input of the first set of one or more inputs and prior to executing the audio meditation function, displaying a fourth user interface that includes a fourth user-interactive graphical user interface object that, when selected, initiates a process for selecting a first audio media item to be played as part of executing the audio meditation function, and
after receiving the second input of the third set of one or more inputs and prior to executing the second function, displaying a fifth user interface that includes a fifth user-interactive graphical user interface object that, when selected, initiates a process for selecting a duration for execution of the second function.

23. The non-transitory computer-readable storage medium of claim 22, the one or more programs further including instructions for:
while displaying the fifth user interface:
displaying a second visual representation of a currently selected duration with a first duration value;

receiving, via the one or more input devices, a fourth set of one or more inputs that includes a third input corresponding to a request to change the currently selected duration; and in response to receiving the third input corresponding to a request to change the currently selected duration, updating the second visual representation of the currently selected duration to be displayed with a second duration value different from the first duration value.

24. The non-transitory computer-readable storage medium of claim 19, the one or more programs further including instructions for:

after displaying the first user interface, receiving a swipe input;

in accordance with a determination that the swipe input was received while the audio meditation function is executing, displaying, via the display generation component, a set of playback controls for modifying media playback of media associated with the second function; and in accordance with a determination that the swipe input was received while the second function is executing, foregoing displaying the set of playback controls.

25. The non-transitory computer-readable storage medium of claim 19, wherein executing the audio meditation function includes concurrently displaying a representation of time that corresponds to execution of the audio meditation function and a second measurement of the first physiological parameter.

26. The non-transitory computer-readable storage medium of claim 19, wherein displaying the second user interface includes displaying, via the display generation component, a third measurement of the first physiological parameter taken during the first amount of cumulative time.

27. The non-transitory computer-readable storage medium of claim 19, the one or more programs further including instructions for:

executing the audio meditation function for a third duration of time; and after executing the audio meditation function for the third duration of time, displaying a first iteration of the second user interface, wherein the first iteration of the second user interface includes a visual representation of the third duration of time.

28. The non-transitory computer-readable storage medium of claim 27, wherein the first iteration of the second user interface includes a sixth user-interactive graphical user interface object for ceasing to display the second user interface, the one or more programs further including instructions for:

receiving a fourth input that corresponds to selection of the sixth user-interactive graphical user interface object for ceasing to display the second user interface; and in response to receiving the fourth input that corresponds to selection of the sixth user-interactive graphical user interface object for ceasing to display the second user interface, returning to the first user interface, wherein returning to the first user interface includes displaying, via the display generation component, the first user interface that concurrently includes:

the first user-interactive graphical user interface object that, when selected, initiates execution of the audio meditation function, wherein the audio meditation function includes measuring, via the one or more sensors, the first physiological parameter; and the second user-interactive graphical user interface object that, when selected, initiates execution of the second function different from the audio meditation function, wherein the second function includes measuring, via the one or more sensors, the second physiological parameter.

29. The non-transitory computer-readable storage medium of claim 28, the one or more programs further including instructions for:

after returning to the first user interface, while displaying the first user interface:

receiving, via the one or more input devices, a fifth set of one or more inputs that includes a fifth input corresponding to the second user-interactive graphical user interface object; and in response to receiving the fifth set of one or more inputs, executing the second function.

30. The non-transitory computer-readable storage medium of claim 29, the one or more programs further including instructions for:

after executing the second function, displaying a second iteration of the second user interface that includes a third visual representation of a third duration of time, wherein the third duration of time includes the first amount of cumulative time that the audio meditation function has been executed within the predetermined time period, and an updated second amount of cumulative time that the second function has been executed during the predetermined time period.

31. The non-transitory computer-readable storage medium of claim 19, the one or more programs further including instructions for:

while executing the audio meditation function:

displaying the third user-interactive graphical user interface object for displaying a workout application; and receiving a sixth input that corresponds to selection of the third user-interactive graphical user interface object for displaying the workout application; and in response to receiving the sixth input that corresponds to selection of the third user-interactive graphical user interface object for displaying the workout application, displaying, via the display generation component, a workout application user interface.

32. The non-transitory computer-readable storage medium of claim 31, the one or more programs further including instructions for:

while executing the audio meditation function:

after displaying the workout application user interface, receiving, via the one or more input devices, a sixth set of one or more inputs that includes a seventh input corresponding to a request to initiate execution of a workout tracking function different from the audio meditation function; and in response to receiving the sixth set of one or more inputs, executing the workout tracking function while continuing execution of the audio meditation function.

33. The non-transitory computer-readable storage medium of claim 32, the one or more programs further including instructions for:

after concurrently executing the audio meditation function and the workout tracking function for a third duration of time:

determining that the audio meditation function has stopped executing;

after determining that the audio meditation function has stopped executing, continuing execution of the workout tracking function for a fourth duration of time; and after continuing execution of the workout tracking function for the fourth duration of time, displaying, via the display generation component, a third iteration of the second user interface that includes a fourth visual representation of a fifth duration of time, wherein the fifth duration of time includes the third duration of time that the audio meditation function has been executed within the predetermined time period without including the fourth duration of time.

34. The non-transitory computer-readable storage medium of claim 19, wherein the first user interface includes a seventh user-interactive graphical user interface object that, when selected, initiates execution of a third function different from the audio meditation function and the second function, wherein the third function includes measuring, via the one or more sensors, a third physiological parameter, the one or more programs further including instructions for:

while displaying the first user interface, receiving, via the one or more input devices, a seventh set of one or more inputs that includes an eighth input corresponding to the seventh user-interactive graphical user interface object; and in response to receiving the seventh set of one or more inputs, executing the third function.

35. The non-transitory computer-readable storage medium of claim 34, the one or more programs further including instructions for:

after executing the third function, displaying a sixth user interface that includes a fifth visual representation of a sixth duration of time, wherein the sixth duration of time includes the first amount of cumulative time that the audio meditation function has been executed within the predetermined time period, the second amount of cumulative time that the second function has been executed during the predetermined time period, and a third amount of cumulative time that the third function has been executed during the predetermined time period.

36. The non-transitory computer-readable storage medium of claim 19, the one or more programs further including instructions for:

displaying a notification corresponding to the second function based on a determination about a current time;

while displaying the notification, receiving, via the one or more input devices, a ninth input corresponding to the notification corresponding to the second function; and in response to receiving the ninth input, displaying a seventh user interface that includes an eighth user-interactive graphical user interface object that, when selected, initiates execution of the second function.

37. A method, comprising:

at a computer system that is in communication with a display generation component, one or more input devices, and one or more sensors:

displaying, via the display generation component, a first user interface that concurrently includes:

a first user-interactive graphical user interface object that, when selected, initiates execution of an audio meditation function; and a second user-interactive graphical user interface object that, when selected, initiates execution of a second function different from the audio meditation function;

receiving, via the one or more input devices, a first set of one or more inputs that includes a first input corresponding to the first user-interactive graphical user interface object;

in response to receiving the first set of one or more inputs:

executing, for a first period of time, the audio meditation function, wherein executing the audio meditation function includes measuring, for the first period of time, via the one or more sensors, a first physiological parameter; and displaying a first measurement of the first physiological parameter during the first period of time;

while executing the audio meditation function, displaying, in an audio meditation user interface, a third user-interactive graphical user interface object for displaying a workout application during the first period of time;

receiving, via the one or more input devices, a second set of one or more inputs that includes selection of the third user-interactive graphical user interface object;

in response to receiving the second set of one or more inputs, executing a workout tracking function while continuing execution of the audio meditation function;

receiving, via the one or more input devices, a third set of one or more inputs that includes a second input corresponding to the second user-interactive graphical user interface object;

in response to receiving the third set of one or more inputs:

executing, for a second period of time, the second function, wherein executing the second function includes measuring, for the second period of time, via the one or more sensors, a second physiological parameter; and foregoing displaying, for the entire duration of the second period of time in which the second physiological parameter is measured, a measurement of the second physiological parameter;

after executing the audio meditation function, displaying a second user interface that includes:

an average measurement of the first physiological parameter measured while executing the audio meditation function for the first period of time; and a visual representation of a first duration of time, wherein the first duration of time includes a first amount of cumulative time that the audio meditation function has been executed within a predetermined time period and a second amount of cumulative time that the second function has been executed during the predetermined time period; and after executing the second function, displaying a third user interface that includes:

an average measurement of the second physiological parameter measured while executing the second function for the second period of time; and a visual representation of a second duration of time, wherein the second duration of time includes an updated first amount of cumulative time that the audio meditation function has been executed within the predetermined time period and an updated second amount of cumulative time that the second function has been executed during the predetermined time period.

38. The method of claim 37, wherein:
displaying the first user interface includes displaying a current time,
executing the audio meditation function includes displaying an audio meditation function user interface that includes an indication of the current time, and
executing the second function includes displaying a second function user interface that does not include the indication of the current time.

39. The method of claim 37, wherein executing the audio meditation function includes causing audio playback, and wherein executing the second function does not include causing audio playback.

40. The method of claim 37, further comprising:
after receiving the first input of the first set of one or more inputs and prior to executing the audio meditation function, displaying a fourth user interface that includes a fourth user-interactive graphical user interface object that, when selected, initiates a process for selecting a first audio media item to be played as part of executing the audio meditation function, and
after receiving the second input of the third set of one or more inputs and prior to executing the second function, displaying a fifth user interface that includes a fifth user-interactive graphical user interface object that, when selected, initiates a process for selecting a duration for execution of the second function.

41. The method of claim 40, further comprising:
while displaying the fifth user interface:
displaying a second visual representation of a currently selected duration with a first duration value;
receiving, via the one or more input devices, a fourth set of one or more inputs that includes a third input corresponding to a request to change the currently selected duration; and
in response to receiving the third input corresponding to a request to change the currently selected duration, updating the second visual representation of the currently selected duration to be displayed with a second duration value different from the first duration value.

42. The method of claim 37, further comprising:
after displaying the first user interface, receiving a swipe input;
in accordance with a determination that the swipe input was received while the audio meditation function is executing, displaying, via the display generation component, a set of playback controls for modifying media playback of media associated with the second function; and
in accordance with a determination that the swipe input was received while the second function is executing, foregoing displaying the set of playback controls.

43. The method of claim 37, wherein executing the audio meditation function includes concurrently displaying a representation of time that corresponds to execution of the audio meditation function and a second measurement of the first physiological parameter.

44. The method of claim 37, wherein displaying the second user interface includes displaying, via the display generation component, a third measurement of the first physiological parameter taken during the first amount of cumulative time.

45. The method of claim 37, further comprising:
executing the audio meditation function for a third duration of time; and
after executing the audio meditation function for the third duration of time, displaying a first iteration of the second user interface, wherein the first iteration of the second user interface includes a visual representation of the third duration of time.

46. The method of claim 45, wherein the first iteration of the second user interface includes a sixth user-interactive graphical user interface object for ceasing to display the second user interface, further comprising:
receiving a fourth input that corresponds to selection of the sixth user-interactive graphical user interface object for ceasing to display the second user interface; and
in response to receiving the fourth input that corresponds to selection of the sixth user-interactive graphical user interface object for ceasing to display the second user interface, returning to the first user interface, wherein returning to the first user interface includes displaying, via the display generation component, the first user interface that concurrently includes:
the first user-interactive graphical user interface object that, when selected, initiates execution of the audio meditation function, wherein the audio meditation function includes measuring, via the one or more sensors, the first physiological parameter; and
the second user-interactive graphical user interface object that, when selected, initiates execution of the second function different from the audio meditation function, wherein the second function includes measuring, via the one or more sensors, the second physiological parameter.

47. The method of claim 46, further comprising:
after returning to the first user interface, while displaying the first user interface:
receiving, via the one or more input devices, a fifth set of one or more inputs that includes a fifth input corresponding to the second user-interactive graphical user interface object; and
in response to receiving the fifth set of one or more inputs, executing the second function.

48. The method of claim 47, further comprising:
after executing the second function, displaying a second iteration of the second user interface that includes a third visual representation of a third duration of time, wherein the third duration of time includes the first amount of cumulative time that the audio meditation function has been executed within the predetermined time period, and an updated second amount of cumulative time that the second function has been executed during the predetermined time period.

49. The method of claim 37, further comprising:
while executing the audio meditation function:
displaying the third user-interactive graphical user interface object for displaying a workout application; and
receiving a sixth input that corresponds to selection of the third user-interactive graphical user interface object for displaying the workout application; and
in response to receiving the sixth input that corresponds to selection of the third user-interactive graphical user interface object for displaying the workout application, displaying, via the display generation component, a workout application user interface.

50. The method of claim 49, further comprising:
while executing the audio meditation function:
- after displaying the workout application user interface, receiving, via the one or more input devices, a sixth set of one or more inputs that includes a seventh input corresponding to a request to initiate execution of a workout tracking function different from the audio meditation function; and
- in response to receiving the sixth set of one or more inputs, executing the workout tracking function while continuing execution of the audio meditation function.

51. The method of claim 50, further comprising:
after concurrently executing the audio meditation function and the workout tracking function for a third duration of time:
- determining that the audio meditation function has stopped executing;
after determining that the audio meditation function has stopped executing, continuing execution of the workout tracking function for a fourth duration of time; and
after continuing execution of the workout tracking function for the fourth duration of time, displaying, via the display generation component, a third iteration of the second user interface that includes a fourth visual representation of a fifth duration of time, wherein the fifth duration of time includes the third duration of time that the audio meditation function has been executed within the predetermined time period without including the fourth duration of time.

52. The method of claim 37, wherein the first user interface includes a seventh user-interactive graphical user interface object that, when selected, initiates execution of a third function different from the audio meditation function and the second function, wherein the third function includes measuring, via the one or more sensors, a third physiological parameter, the method further comprising:
while displaying the first user interface, receiving, via the one or more input devices, a seventh set of one or more inputs that includes an eighth input corresponding to the seventh user-interactive graphical user interface object; and
in response to receiving the seventh set of one or more inputs, executing the third function.

53. The method of claim 52, further comprising:
after executing the third function, displaying a sixth user interface that includes a fifth visual representation of a sixth duration of time, wherein the sixth duration of time includes the first amount of cumulative time that the audio meditation function has been executed within the predetermined time period, the second amount of cumulative time that the second function has been executed during the predetermined time period, and a third amount of cumulative time that the third function has been executed during the predetermined time period.

54. The method of claim 37, further comprising:
displaying a notification corresponding to the second function based on a determination about a current time;
while displaying the notification, receiving, via the one or more input devices, a ninth input corresponding to the notification corresponding to the second function; and
in response to receiving the ninth input, displaying a seventh user interface that includes an eighth user-interactive graphical user interface object that, when selected, initiates execution of the second function.

* * * * *